(12) United States Patent
Armand et al.

(10) Patent No.: US 8,563,761 B2
(45) Date of Patent: Oct. 22, 2013

(54) BORON OR ALUMINUM COMPLEXES

(75) Inventors: Michel Armand, Paris (FR);
Jean-Marie Tarascon, Mennecy (FR);
Nadir Recham, Amiens (FR); Sylvie Grugeon, Feuquieres (FR); Stephane Laruelle, Saveuse (FR); Shanmukaraj Devaraj, Amiens (FR)

(73) Assignees: Centre National de la Recherche, Paris (FR); Universite de Picardie Jules Verne, Amiens (FR)

( * ) Notice: Subject to any disclaimer, the term of this patent is extended or adjusted under 35 U.S.C. 154(b) by 327 days.

(21) Appl. No.: 12/736,195

(22) PCT Filed: Mar. 19, 2009

(86) PCT No.: PCT/FR2009/000290
§ 371 (c)(1), (2), (4) Date: Mar. 28, 2011

(87) PCT Pub. No.: WO2009/122044
PCT Pub. Date: Oct. 8, 2009

(65) Prior Publication Data
US 2011/0171112 A1    Jul. 14, 2011

(30) Foreign Application Priority Data
Mar. 19, 2008  (FR) ..................... 08 01506

(51) Int. Cl.
*C07F 5/06*   (2006.01)
*C07F 5/02*   (2006.01)
*C01G 49/02*  (2006.01)

(52) U.S. Cl.
USPC ............. 556/175; 564/11; 558/289; 558/290; 423/472

(58) Field of Classification Search
USPC .................... 564/11; 558/289, 290; 556/175; 423/472
See application file for complete search history.

(56) References Cited

U.S. PATENT DOCUMENTS

| | | | |
|---|---|---|---|
| 2,909,560 | A | 10/1959 | McManimie |
| 3,009,791 | A | 11/1961 | Emrick |
| 4,985,305 | A | 1/1991 | Schubart et al. |
| 6,022,643 | A | 2/2000 | Lee et al. |
| 7,217,842 | B2 | 5/2007 | Schanen et al. |

FOREIGN PATENT DOCUMENTS

| | | |
|---|---|---|
| JP | 59136364 | 8/1984 |
| JP | 8048839 | 2/1996 |

OTHER PUBLICATIONS

Brink et al., Journal of Solid State Chemistry, vol. 155, No. 2, pp. 359-365 (2000).*
International Search Report dated Oct. 1, 2009.

* cited by examiner

*Primary Examiner* — Porfirio Nazario Gonzalez
(74) *Attorney, Agent, or Firm* — Sofer & Haroun, LLP

(57) ABSTRACT

The present invention relates to boron and aluminum complexes, to the preparation thereof, and to the use thereof for solubilizing ionic compounds. The complexes have one of the following formulae:

in which D represents B or Al; $R^1$ represents R, $R_F$, $NO_2$, CN, C(=O)OR, $RSO_2$, or $R_FSO_2$; $-X^1-$, $-X^2-$, $-X^3-$ and $X_4$ each represent a divalent group $>C=O$, $>C=NC\equiv N$, $>C=C(C\equiv N)_2$, $>CR^2R^3$ or $>SO_2$; $-Y^1-$, $-Y^2-$ and $-Y^3-$ each represent a divalent group $-O-$, $>N(C\equiv N)$, $>N(COR_F)$, $>N(SO_2R^4)$, $>NR^4$, $>N(COR^4)$ or $>N(SO_2R_F)$; R, $R^2$ and $R^3$ each represent H, an alkyl group, an aryl group, an alkylaryl group, an arylalkyl group, an oxaalkyl group or an alkenyl group; $R^4$ represents an alkyl group, an aryl group, an alkylaryl group, a heteroaryl group, an arylalkyl group, an oxaalkyl group, an alkenyl group or an $R_FCH_2-$ group; $R_F$ is a perfluoroalkyl group, a partially fluorinated alkyl group, or a partially or totally fluorinated phenyl group; each of the $R'^2$ and $R'^3$ groups represents R or F.

19 Claims, 1 Drawing Sheet

BORON OR ALUMINUM COMPLEXES

RELATED APPLICATIONS

This application is a National Phase application of PCT/FR2009/000290, filed on Mar. 19, 2009, which in turn claims the benefit of priority from French Patent Application No. 08 01506, filed on Mar. 19, 2008, the entirety of which are incorporated herein by reference

BACKGROUND

1. Field of the Invention

The present invention relates to boron and aluminum complexes, to the preparation thereof and to the use thereof for solubilizing ionic compounds.

2. Description of Related Art

Many compounds of use for performing nucleophilic substitutions which make it possible to modify materials and molecules in inorganic chemistry or in organic chemistry are known. Mention may in particular be made of compounds which have an $F^-$, $OCN^-$, $O^{2-}$, $O_2^{2-}$, $O_2^{\cdot-}$, $OH^-$, $RO^-$, $N_3^-$, $CN^-$, $HNCN^-$, or $NCN^{2-}$ anion. Fluorinated compounds and isocyanates are particularly advantageous for the polymer or refrigeration agent industry, for surface treatment, or for pharmaceutical or agrochemical products. However, the nucleophilic substitution reactions using these compounds are impossible in protic solvents, such as, for example, $H_2O$, $CH_3OH$, formamide and N-methylformamide, which are capable of dissolving the salts of said anions, since the very strong solvation of the abovementioned anions reduces their nucleophilic nature. In addition, when a compound of one of the abovementioned anions is brought into contact with lamellar inorganic structures of FeOCl or TiNCl type, there is a greater risk of exfoliation owing to penetration of the ion in solvated form between the sheets. In polar aprotic solvents, the reactivity of the abovementioned anions is limited by the very low solubility of the corresponding alkali metal or alkaline-earth metal salts. Another problem comes from the basicity of said anions, the charge of which is concentrated in a small volume ($r_{F^-}=r_{OH^-}=r_{O^{2-}}=1.4$ Å), which promotes the reaction in which protons in the α-position are eliminated in organic chemistry reactions, thereby prohibiting substitutions on sensitive substrates. The elimination in the β-position (Hoffmann degradation) limits the stability of the quaternary ammonium cations on quite long chains so as to induce solubility in aprotic solvents.

Catalysts which are more thermally stable than quaternary ammoniums have been proposed, in particular in U.S. Pat. No. 7,217,842 or by A. Pleschke, et al. Röschenthaler Journal of Fluorine Chemistry, Volume 125, No. 6, June 2004, pages 1031-1038. These onium salts only minimally reduce the temperature at which Halex reactions are carried out and do not solve the problem of eliminations on sensitive substrates.

One proposed solution for increasing the solubility of the alkali metal or alkaline-earth metal salts of the abovementioned anions in aprotic solvents consists in complexing the alkali metal or alkaline-earth metal cations with a complexing agent chosen, for example, from diglymes, triglymes, tetraglymes, crown ethers and cryptates. The use of these agents actually makes it possible to increase the solubility of the above-mentioned salts in aprotic solvents. However, the rate of the elimination reactions is greatly increased and, consequently, these additives are only of slight interest. In addition, the most effective complexing agents for increasing solubility are expensive compounds, in particular crown ethers and cryptates. As a result, the use of complexing agents has not given rise to major industrial developments.

In practice, exchange reactions between chlorine and fluorine are carried out at very high temperatures in solvents such as sulfolane (tetramethylenesulfone). For example, with potassium fluoride (Halex process), the exchange reaction is carried out at temperatures of from 200° C. to 300° C., with low yields in terms of materials and high energy costs.

No industrial preparation of isocyanates from metal cyanates or industrial preparations from $O^{2-}$, $O_2^{2-}$, $O_2^{\cdot-}$, $HNCN^-$ and $NCN^{2-}$ anions are known. The $OH^-$, $RO^-$, $CN^-$, and $N_3^-$ anions are used for nucleophilic substitution reactions, but the yields are low owing to the competing elimination reactions.

It is known that Lewis acids such as $BF_3$ and $PF_5$ are capable of complexing fluorine ions so as to give the coordination anions $BF_4^-$ and $PF_6^-$, the corresponding metal salts of which are readily soluble in polar aprotic solvents. However, the salts of the $BF_4^-$ and $PF_6^-$ anions have no nucleophilic power for performing substitutions, for example, of a chlorine atom with a fluorine atom, owing to the large amount of energy of the Lewis acid ⇔ a base interaction. On the contrary, the salts of these anions are used when a strictly non-nucleophilic and non-complexing anion is required, in order to stabilize unstable cationic species or as a support electrolyte in electrochemistry. Also known are triphenylboron derivatives, in particular the fluorinated derivative $(C_6F_5)_3B$ which is a powerful Lewis acid capable of complexing LiF despite the high reticular energy of this salt. $(C_6F_5)_3BF^-$ anions, like $BF_4^-$ and $PF_6^-$, are not nucleophiles allowing fluorine exchange. In addition, these compounds are difficult to obtain and they are extremely expensive.

U.S. Pat. No. 2,909,560 describes a process for preparing a cyclic boron compound, 2,6,7-trioxa-1-bora-4-methylbicyclo[2.2.2]octane, by reacting 1,1,1-trimethylethane (I) with boric acid $H_3BO_3$ (II), and the use of said cyclic compound as a stabilizer of polyethylene.

OBJECTS AND SUMMARY

The objective of the present invention is to provide a complex capable of forming an adduct with a salt, said adduct having a nucleophilic anionic part and being soluble in polar aprotic solvents.

The invention is based essentially on the fact that, unexpectedly, complexes formed with a Lewis acid derived from boron or from aluminum are capable of forming complexes with a Z anion, chosen from $F^-$, $OCN^-$, $O^{2-}$, $O_2^{2-}$, $O_2^{\cdot-}$, $OH^-$, $RO^-$, $RN^{2-}$, $R_2N^-$ and $CN^-$, $HNCN^-$, $NCN^{2-}$ and $N^{3-}$, of a salt of which the cation may be an alkali metal cation ($Li^+$, $Na^+$, $K^+$, $Rb^+$, $Cs^+$), an alkaline-earth metal cation ($Mg^{++}$, $Ca^{++}$, $Sr^{++}$, $Ba^{++}$), an $Ag^+$ or $Pb^{++}$ cation, or an onium cation (ammonium, phosphonium, sulfonium, iodonium, pyridinium or imidazolium). The adducts thus formed have a marked nucleophilic nature capable of allowing substitutions on organic or inorganic substrates, and also a reduced basicity making it possible to treat substrates sensitive in particular to elimination. The adducts have an increased solubility in polar aprotic solvents. In addition, when the cation of the adduct is an onium cation, the adduct can have a melting point below 100° C., and it can be used as an ionic liquid.

The subject of the present invention is boron or aluminum complexes, adducts formed by said complexes with an ionic compound, and various uses of the complexes and of the adducts.

The boron or aluminum complexes according to the present invention are tricyclic to compounds corresponding to one of the general formulae:

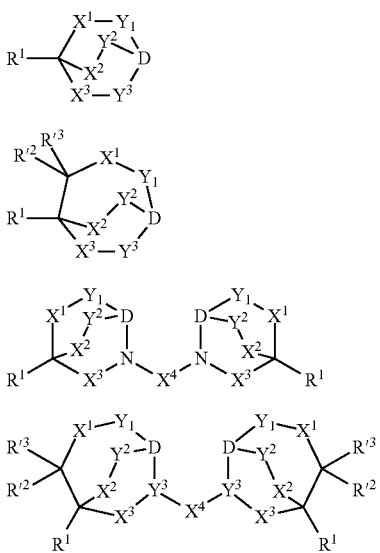

(ID)

(IID)

(IIID)

(IVD)

in which:

D represents boron B or aluminum Al;

$R^1$ represents R, $R_F$, $NO_2$, CN, C(=O)OR, $RSO_2$, or $R_FSO_2$;

each of the —$X^1$—, —$X^2$—, —$X^3$— and $X_4$ groups represents, independently of the others, a >C=O, >C=NC=N, >C=C(C=N)$_2$, >CR$^2$R$^3$ or >SO$_2$ divalent group;

each of the —$Y^1$—, —$Y^2$— and —$Y^3$— groups represents, independently of the others, an —O—, >N(C=N), >N(COR$_F$), >N(SO$_2$R$^4$), >NR$^4$, >N(COR$^4$) or >N(SO$_2$R$_F$) divalent group;

R, $R^2$ and $R^3$ each represent, independently of the others, H, an alkyl group, an aryl group, an alkylaryl group, an arylalkyl group, an oxaalkyl group or an alkenyl group;

$R^4$ represents an alkyl group, an aryl group, an alkylaryl group, a heteroaryl group, an arylalkyl group, an oxaalkyl group, an alkenyl group or an $R_F$—CH$_2$— group;

$R_F$ is a perfluoroalkyl group or a partially fluorinated alkyl group (in which preferably at least 60% of the hydrogen atoms are replaced with fluorine atoms), preferably containing from 1 to 8 carbon atoms, or a partially or completely fluorinated phenyl group;

each of the $R'^2$ and $R'^3$ groups represents R or F; it being understood that:

several R or $R_F$ groups can be linked together so as to form a segment of an oligomer or of a polymer;

in a ID and IID complex, if two groups among —$X^1$—, —$X^2$— and —$X^3$— each represent >C=O, then the third group represents a >CR$^2$R$^3$ group;

in a IB complex, if each of the $X^1$, $X^2$ and $X^3$ groups is a CH$_2$ group and each of the Y groups is O, then $R^1$ is other than CH$_3$.

In the remainder of the present text:

"X groups" denotes collectively the groups $X^1$, $X^2$, $X^3$ and $X^4$, and "$X^i$ group" denotes any one among the groups $X^1$, $X^2$, $X^3$ and $X^4$; "Y groups" denotes collectively the groups $Y^1$, $Y^2$ and $Y^3$, and "$Y^i$ group" denotes any one among the Y groups.

The alkyl or alkenyl groups which can be chosen for the $R^1$ to $R^4$ and R substituents preferably contain at most 22 carbon atoms, and the aryl groups are preferably phenyl groups optionally bearing one or more alkyl groups containing from 1 to 12 carbon atoms, one or more $CF_3$ or $OCF_3$ groups, a CN group or an $NO_2$ group.

The heteroaryl groups which can be chosen for $R^4$ are preferably pyridinyl, pyrazinyl, pyridazinyl or pyrimidyl groups, said groups optionally bearing one or more alkyl groups containing from 1 to 12 carbon atoms, one or more $CF_3$ or $OCF_3$ groups, a CN group or an $NO_2$ group.

The Lewis acid nature of the compounds of the invention can be modulated through the choice of the $R^1$ group, of the X groups and of the Y groups. The various groups are classified hereinafter in decreasing order:

—$R^1$: $R_FSO_2$—, —$NO_2$, $RSO_2$— ≈ —CN, —C(=O)OR, —OR, R—

>X: >C=C(C=N)$_2$, >C=NC=N, >SO$_2$, >C=O, >CH$_2$>CR$^2$R$^3$

>Y: >N(SO$_2$R$_F$), >N(COR$_F$)≈>N(SO$_2$R$^4$), >N(C=N), >NCOR$^4$, >O, >NR$^4$.

When D represents boron, the I-D, II-D, III-D and IV-D complexes are denoted, respectively, by I-B, II-B, III-B and IV-B. The boron complexes are stable with respect to water and alcohols and are soluble in most polar organic solvents.

When D represents Al, the I-D, II-D, III-D and IV-D complexes are denoted, respectively, by I-Al, II-Al, III-Al and IV-Al. The aluminum complexes are water-hydrolysable, except those in which the three —X— groups are other than >CR$^1$R$^2$.

A boron or aluminum complex according to the present invention can be used advantageously as a complexing agent with an $M_zZ'_m$ salt in which M is a cation of which the valence n is from 1 to 3, and Z' is an anion of which the valence z' is 1 or 2. When Z' is monovalent, it is chosen from the following Z anions: F$^-$, OCN$^-$, $O_2^{\cdot -}$, OH$^-$, RO$^-$, $N_3^-$, $R_2N^-$, CN$^-$, HNCN$^-$, [$O^{2-}M'^+$]$^-$, [$O_2^{2-}M'^+$]$^-$ and [$NCN^{2-}M'^+$]. When Z' is divalent, it is chosen from the following Z'' anions: $O^{2-}$, $O_2^{2-}$ and $NCN^{2-}$. M represents an alkali metal cation, an alkaline-earth metal cation, Ag$^+$, Pb$^{2+}$, an yttrium cation, a lanthanum cation or an organic cation. The organic cation can be chosen from ammonium, phosphonium, tetrakis(dialkylamino)phosphonium, bis[tris(dialkylamino)]diphosphonioazenium, sulfonium, pyridinium, amidinium, guanidinium, imidazolium, pyrazolium and triazolium cations, said organic cations optionally bearing a substituent chosen from alkyl, oxaalkyl, aryl (in particular phenyl), alkylaryl (in particular alkylphenyl) and arylalkyl (in particular phenylalkyl) groups, and it being possible for said cations to be linked to one another via an organic linker, so as to form oligomers or polymers. M' is chosen from H and the monovalent cations cited via M. In the remainder of the text, "I/MZ'", "IID/MZ'", "IIID/MZ'" and "IVD/MZ'" denote an $M_zZ'_m$ salt complexed, respectively, with a ID, IID, IIID or IVD of the present invention. The aluminum complexes can form adducts not only with a salt of the abovementioned anions, but also with a salt of the Cl$^-$, Br$^-$, $S^{2-}$ or $S_2^{2-}$ anion.

A mononuclear aluminum complex ID or IID forms adducts not only in the [(Al)—Z]–M$^+$ form, but also in a trinuclear form of the [(Al)—Z(Al)]$^-$M$^+$ type having the sequence Al—Z—Al through involvement of the "d" orbitals of aluminum, which do not exist in the case of boron. The III-B, IV-B, III-Al and IV-Al complexes are binuclear and the B—Z—B and Al—Z—Al bonds make an angle of between 60 and 150° C.

An adduct according to the present invention can be represented by one of the following formulae, in which the various elements have the meaning given above.

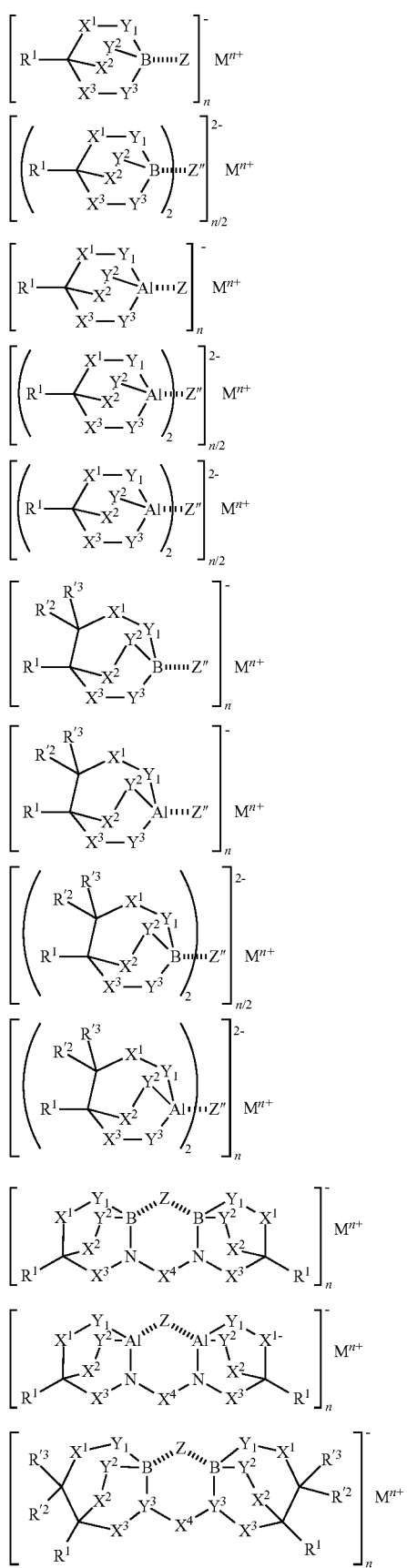

Among the complexes of the invention, those in which each of the Y groups represents O are advantageous owing to the fact that they can be readily obtained from a triol. They are denoted hereinafter by B-a for the boron complexes and Al-a for the Al complexes. The relatively weak acid nature provided by the three O atoms chosen for the Y groups can be increased through the choice of X groups providing a stronger acid nature, for example >C=O, >C=NC=N, >C=C(C=N)$_2$ or SO$_2$. It is preferable for just one of the X groups to be an SO$_2$ group. The acid nature can also be increased through the choice of a strongly electron-withdrawing R$^1$ group, for example R$_F$SO$_2$—, NO$_2$, RSO$_2$—, —CN, or —C(=O)OR.

The complexes in which the three Y groups are nitrogenous groups are denoted hereinafter by B-c for the boron complexes and Al-c for the Al complexes, and those which contain at least one nitrogenous Y group and at least one Y group which is oxygen are denoted by B-b for the boron complexes and Al-b for the Al complexes.

The complexes of the invention in which at least one Y group is an NR$^4$ group, in particular when the 3 Y groups are NR$^4$ groups, preferably have X groups chosen from >C=O, >C=NC=N and >C=C(C=N)$_2$ groups.

The complexes of the invention in which at least one of the Y groups is other than NR$^4$ and contains a nitrogen atom and the complexes in which at least one of the Y groups to is an NR$^4$ group in which R$^4$ is an aryl or heteroaryl group bearing at least one withdrawing group (for example, CN, NO$_2$, CF$_3$) have a strong Lewis acid nature, and as a result they have a solubility in aprotic solvents which is greater than that of the similar complexes in which all the Y groups are O. Their Lewis acid nature can be modulated through:

the particular choice of the Y groups containing a nitrogen atom;
the choice of the X groups and/or the R group;
the number of Y groups containing a nitrogen atom.

The complexes in which the three Y groups are groups containing a nitrogen atom have the strongest acid nature.

The B-b, B-c, Al-b and Al-c complexes, and also the adducts thereof, are as a result particularly advantageous as a battery electrolyte additive.

Among the boron complexes and the aluminum complexes of the invention, those in which each of the X groups represents $CH_2$ are readily obtained by insertion of formaldehyde $H_2C=O$ into a —CH bond so as to form —$CCH_2OH$ and they introduce only a minimum steric hindrance, in particular those in which each of the three X groups represents $CH_2$. The complexes in which X is $CHR^2$ are obtained in the same manner from the aldehyde $R^2CH=O$.

The relatively poorly electron-withdrawing nature provided by the three $CH_2$ groups chosen for the X groups can be increased through the choice of Y groups providing a stronger acid nature, for example an >$N(SO_2CF_3)$, >$N(COCF_3)$, >$N(SO_2R)$ or >$N(C\equiv N)$ group, or an >$NR^4$ group in which $R^4$ is an aryl or heteroaryl bearing at least one withdrawing group (for example, CN, $NO_2$, $CF_3$, $OCF_3$) and/or through the choice of a strongly electron-withdrawing $R^1$ group, for example $R_FSO_2$—, $NO_2$, $RSO_2$—, —CN or —$C(=O)OR$.

A particular category of complexes and adducts comprises those in which each of the >X groups represents >$CH_2$ and the Y groups are identical and each contain a nitrogen atom. The presence of the nitrogen atom confers, on the complexes and on the corresponding adducts, a greater solubility in the abovementioned polar solvents, in less polar solvents such as acetonitrile, ketones, glymes or benzonitrile, and for the onium salts, dichloromethane and α,α,α-trifluorotoluene, and in ionic liquids, compared with the complexes and with the adducts in which Y is O.

The complexes in which —$X^1$— and —$X^2$— represent >$CH_2$ and >$X^3$ represents >C=O, C=NCN or C=$C(CN)_2$ are advantageous since they allow the formation of adducts with a salt of the $Z^-$ anion and of a cation of an alkali metal such as Na and K, a fortiori with a salt of an onium, said adducts being soluble in polar solvents such as dimethylformamide (DMF), dimethylacetamide (DMAc), N-methylpyrrolidone (NMP) or sulfolane and polar ionic liquids such as ethylmethylimidazolium bis(trifluorosulfonimide) (EMI-TFSI), and which readily exchange the $Z^-$ anion when they are in the presence of substrates which have a leaving group.

The complexes in which at least one of the X groups is a nitrogenous group such as C=NCN and C=$C(CN)_2$ are useful as an additive in the electrolyte of a lithium battery, since they are capable of readily forming an adduct with LiF, despite the large amount of reticular energy of this salt.

Another category of complexes and adducts comprises those in which $R^1$ is $C_2H_5$ and which are derived from $C_2H_5C(CH_2OH)_3$. The asymmetry introduced by the ethyl group increases the solubility of the complexes and of the adducts in polar solvents, in particular in the abovementioned solvents.

The Al-a complexes (i.e. those in which each of the Y groups is O) in which either one of the X groups is >CO and each of the other two >X groups is >$CH_2$, or one >X group is >$CH_2$ and the other two >X groups are each >CO, have a tendency to be in equilibrium with oligomeric species in which the aluminum takes on a coordination of between 5 and 6, thereby reducing the solubility of the monomeric species IAl.

The aluminum complexes in which the X groups are $CR^2R^3$ groups in which one of $R^2$ and $R^3$ is other than H, owing to the steric hindrance, are more soluble and tend to be monomeric. The same is true of the aluminum complexes in which the X or Y groups contain a nitrogen atom.

The boron and aluminum complexes of the present invention are useful for various applications. A complex according to the invention can be used directly as an additive of an electrolyte or for the preparation of an adduct with an MZ salt, said adduct being useful in particular in various nucleophilic substitution reactions.

The solubility of the B/MZ and Al/MZ adducts in nonprotic or nonprotogenic solvents, generally called aprotic solvents, is greater than that of the $M_zZ'$ compounds, in particular the $M_zZ'$ compounds used in lithium batteries. This property is particularly useful when Z' is $F^-$, $O^{2-}$ or $O_2^{2-}$. One category of aprotic solvents is made up of solvating polymers such as polyethers, in particular poly(ethylene oxide).

In a lithium battery, the electrolyte contains a lithium salt, and the cathode contains a compound of a transition metal. Iron and manganese are particularly useful owing to their natural abundance, in the corresponding oxides $Fe_3O_4$, $Fe_2O_3$, MnO and $Mn_3O_4$ The fluoride $CuF_2$ is advantageous for the very positive potential that it gives by reaction with lithium.

Increasing the solubility of the lithium compounds LiF, $Li_2O$ and $Li_2O_2$ makes it possible to improve the rechargeability of displacement electrodes operating according to the reaction equation

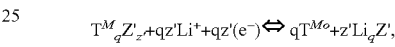

in which $T^M$ is a transition metal of which the valence q is from 2 to 6, and z' is the valence of the Z' anion. The solubility of $Li_2O_2$ is most particularly advantageous in lithium-air batteries in which the reaction of the positive electrode is written $2Li^+ + O_2 + e^- \Leftrightarrow Li_2O_2$. These batteries have a very high capacity per unit of volume and weight, but they suffer from an excessive polarization of more than one volt between the discharge (2.8 V) and the recharge (4.5 V). The solubilization of the peroxide $Li_2O_2$ by complexation with a compound of the invention makes it possible to decrease this overvoltage, which goes to 3.5 V in recharge. A boron or aluminum complex of the present invention is consequently useful as an additive for the electrolyte of a lithium battery. The complex can be used directly, or in the form of an adduct with a salt preferably having an F, $O^{2-}$ or $O_2^{2-}$ anion.

An adduct according to the present invention can be used in various nucleophilic substitution reactions on liquid or solid inorganic compounds, or on organic compounds. According to one embodiment, the adduct is introduced directly into the reaction medium. According to another embodiment, a boron or aluminum complex and an MZ reactant are introduced into the reaction medium, and the adduct is formed in situ. In both cases, the adduct or the complex can be introduced in a stoichiometric or catalytic amount. When the substrate is sensitive to bases, it is recommended to use stoichiometric proportions, since the solution then contains the Z or Z" anions only in the form of adducts, which are a less basic form than the free anions.

In the other cases, use in catalytic amounts is an economic advantage and an advantage in terms of saving of atoms. The boron or aluminum complexes of the present invention are useful for modifying inorganic solid compounds by nucleophilic substitution, by means of "mild chemistry" processes. They are useful in particular for replacing, in various inorganic compounds, the $Cl^-$ or $Br^-$ ion with a Z' anion of which the valence z' is 1 or 2, chosen from $F^-$, $OCN^-$, $O^{2-}$, $[O^{2-}M^{'+}]^-$, $O_2^{2-}$, $[O_2^{2-}M'O^+]-$, $O_2^{.-}$, $OH^-$, $RO^-$, $N_3^-$, $CN^-$, $NCN^{2-}$ and $[NCN^{2-}M^{'+}]^-$.

The replacement of $Cl^-$ or $Br^-$ with $F^-$ in an inorganic compound with a lamellar structure, such as FeOCl, VOCl, BiOCl, $BiONO_3$, TiNCl, TiNBr, ZrNCl or ZrNBr, is impossible in media capable of dissolving fluorides, such as the protic solvents mentioned above, since, in addition to the weak nucleophilic nature of solvated F⁻, the lamellar structures are exfoliated through the action of these solvents. The use of an adduct formed between an MZ reactant and a complex of the invention is a means which allows easy modification of the abovementioned lamellar compounds by nucleophilic substitution, in particular FeOCl and BiONO₃. A process consisting in reacting, in an aprotic organic solvent, a chlorinated or brominated inorganic compound with an MZ reactant in the presence of a IB or IAl complex of the present invention, or with an adduct formed between MZ and the complex, constitutes another subject of the present invention.

In the event that the nucleophilic substitution reactant is an $M_zZ$ salt of a monovalent cation M, the modification reactions would be, respectively:

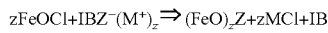

$zFeOCl+IBZ^-(M^+)_z \Rightarrow (FeO)_zZ+zMCl+IB$

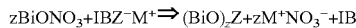

$zBiONO_3+IBZ^-M^+ \Rightarrow (BiO)_zZ+zM^+NO_3^-+IB$

The inorganic compounds obtained by replacement of Cl or Br with Z, in particular the FeOZ compounds in which Z⁻ is F⁻, CN⁻ or OCN⁻, are host structures for lithium, according to the reaction $FeOZ+xLi^++xe^- \Leftrightarrow Li_xFeOZ$. They are consequently useful in the electrochemical storage field. In particular, FeOF has a very high capacity per unit weight (284 Ah/kg) at the potential of 2.5 V vs. Li⁺/Li°, which makes it an advantageous candidate for lithium batteries, with electrolytes constituted of a solution of a lithium salt in a polar organic liquid or in a solvating polymer of polyether type.

In addition, the FeOZ compounds in which Z⁻ is F⁻, CN⁻ or OCN⁻, in particular in the form of insertion compounds with ferrocene, N,N,N'N'-tetramethylphenylenediamine, tetrakis(dimethylaminoethylene) or pyridine, have magnetic properties that are useful in the information storage field.

A BiOF compound is useful as electrode material operating according to a 3-electron redox process, according to the reaction scheme:

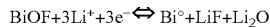

$BiOF+3Li^++3e^- \Leftrightarrow Bi°+LiF+Li_2O$

An adduct according to the present invention can also be used for converting an inorganic compound containing S-L or P-L bonds into a compound containing S—F, P—F, S—CN or P—CN. This application is particularly advantageous for the compounds $\{[CF_3SO_2NSO_2Cl]^-\}_nM^{n+}$, $\{[(ClSO_2)_2N]^-\}_n M^{n+}$ and $\{[(Cl_2PO)_2N]^-\}_nM^{n+}$, which are advantageous sources of the salts $\{[CF_3SO_2NSO_2F]^-\}_nM^{n+}$, $\{[(FSO_2)_2N]^-\}M^{n+}$ and $\{[(F_2PO)_2N]^-\}_nM^{n+}$ which are useful as components of ionic liquids and as electrolytes for lithium batteries. The salt of M can be formed in situ through the action of $[(ClSO_2)_2N]H$ for example on $MF_n$.

In organic, pharmaceutical or macromolecular chemistry, the use of the complexes and of the adducts of the invention is particularly advantageous for modifying aliphatic or aromatic organic compounds (hereinafter denoted "substrates") which have a C-L bond in which C is carbon and L is a halogen (chosen from Cl, Br and I), a pseudohalogen (for example SCN), an ester group —OSO₂R' or an —N(SO₂R')₂ group (in which R' is an alkyl group, an alkylaryl group or a perfluoroalkyl group). The modification consists in converting the C-L bond into a C—F, C—NCO, C—OCN, C—O⁻, C—O—C (ether), C—OO⁻, C—O—O—C, C—OH, C—OR, C—N₃ or C—CN bond. The use of the compounds according to the invention makes it possible to avoid the presence of activating groups which are necessary in the exchange processes of the prior art, and consequently eliminates the additional steps of elimination of these activating groups. Compared with the Halex process, the use of the compounds of the present invention for carrying out a chlorine-fluorine exchange is very advantageous because it makes it possible to use solvents with a lower boiling point, in particular DMF, N-methylpyrrolidinone, N-methylimidazole or even acetonitrile, and the yields are improved. A boron or aluminum complex of the present invention is consequently useful as an agent for complexing a reactant intended for replacing the L anion of a substrate with a Z anion. For this application, the boron compounds IB are particularly preferred. The ionic liquids which do not themselves exhibit a vapor pressure are advantageous for uses at a higher temperature and especially when the product of the reaction is volatile, which allows easy separation or even a continuous process.

The strongly nucleophilic nature of F in a B/MZ adduct or an Al/MZ adduct in which Z is F can be used to benefit in organic chemistry for deprotection reactions when trialkylsilane groups are present in the substrate molecule. Such an adduct advantageously replaces tetrabutylammonium fluoride trihydrate which is generally used, which is expensive, and which introduces very hydrophobic cations, making it difficult to purify the reaction mixtures and introducing prejudicial water in the case of compounds sensitive to hydrolysis. An adduct according to the invention is consequently useful as an agent for deprotecting a trialkylsilyl group. Particularly advantageous for this application are the adducts of alkali metal fluorides or of onium salts of low molecular weight, in particular tetramethylammonium or tetraethylammonium salts and ethylmethylimidazolium salts, used in stoichiometric or catalytic amounts.

Another subject of the invention consists of the processes for preparing the complexes of the invention, and also the D/MZ adducts.

In general, a I-D, II-D, III-D or IV-D complex can be obtained by mixing a compound which is a source of the element D with an organic precursor of the complex comprising a bond —Y—H or —Y-M¹ which is an alkali metal.

The boron-source compound is advantageously chosen from boric acid $B(OH)_3$, an ester $B(OR^5)_3$ ($R^5$ being an alkyl group), an alkali metal or alkaline-earth metal borate $M^2(BO_2)_n$ or $M^2{}_2(B_4O_7)_{/4}$, a boron halide, a boron acetate, or an adduct of a boron halide such as $M^2(BF_4)_n$, n being equal to 1 or 2 depending on whether $M^2$ is monovalent or divalent.

In a 1st embodiment, an ester $B(OR^5)_3$ ($R^5$ being an alkyl group) or boric acid $B(OH)_3$ is mixed with an organic precursor of the complex comprising a —Y—H bond, and the IB complex is obtained, with elimination of alcohol R"OH or of water. For example, a IB-a complex in which each of the three X groups is a $CR^2R^3$ group is obtained by reaction of the triol $R^1C[CR^2R^3OH]_3$ with boric acid $B(OH)_3$ or a lower alkyl borate, in a polar protic solvent, for example ethanol or methanol. $R^1$ may be an alkyl group, an $NO_2$ group, a perfluoroalkylsulfonyl group or a perfluoroaryl group.

In a 2nd embodiment, a precursor of the complex comprising a —Y—H bond is mixed with a borate $M^2(BO_2)_n$ or $M^2{}_2(B_4O_7)_{n/4}$, in the presence of an acid, with formation of a —Y—B bond, and a IB complex and the alkali metal or alkaline-earth metal salt of the acid are obtained.

In a 3rd embodiment, the precursor of the complex in which Y is present in the form of a —YM" bond is mixed with a calculated amount of an acid in the presence of boric acid, of a boron ester or of a borate $M^2(BO_2)_n$ or $M^2{}_2(B_4O_7)_{n/4}$. Advantageously, the acid is chosen in such a way as to form, with M", a salt that is insoluble in the reaction medium. In one particular embodiment, the anion of the acid is chosen such that the salt that it forms with M" directly forms the adduct of the invention.

In a 4th embodiment, a precursor of the complex comprising a —YH bond is mixed with a boron halide, a boron acetate in the presence of a base, or an adduct of a boron halide such as $M^2(BF_4)_n$.

In a 5th embodiment, a precursor of the complex comprising a —Y-M' bond is mixed with a boron halide, a boron acetate or $M^2(BF_4)_n$.

The aluminum-source compound is advantageously chosen from:
- aluminum alkoxides $Al(OR^6)_3$ in which $R^6$ is an alkyl group, preferably branched so as to limit the degree of polymerization of these alkoxides and therefore promote their solubility and their reactivity;
- the compounds $AR^7_3$ in which $R^7$ is preferably an ethyl, propyl, butyl, isobutyl, amyl, isoamyl, hexyl or octyl group (alkylaluminum) or a phenyl group (arylaluminum);
- dialkylamidoaluminums $Al(NR^8_2)_3$ in which $R^8$ is an alkyl group, preferably $CH_3$ or $C_2H_5$;
- aluminum halides, preferably $AlCl_3$, $AlF_3$ or $AlBr_3$;
- aluminum hydroxide.

In a 1st embodiment, the aluminum complex is prepared in an anhydrous polar solvent by reacting a precursor of the complex comprising a —YH group with an aluminum alkoxide $Al(OR^6)_3$. Aluminum isopropoxide and aluminum tert-butoxide are particularly preferred.

In a 2nd embodiment, the aluminum complex is prepared by reacting a precursor of the complex having a —YH bond with an alkylaluminum or an arylaluminum $AR^7_3$ in which $R^7$ is preferably an ethyl, propyl, butyl, isobutyl, amyl, isoamyl, hexyl, octyl or phenyl group.

In a 3rd embodiment, the aluminum complex is prepared by reacting a precursor of the complex having a —YH bond with a dialkylamidoaluminum $Al(NR^8_2)_3$ in which $R^8$ is $CH_3$ or $C_2H_5$.

In a 4th embodiment, the aluminum complex is prepared by reacting a precursor of the complex having a —Y-M¹ bond ($M^1$ preferably being an alkali metal) with an aluminum salt, in particular an aluminum halide $AlCl_3$ and $AlBr_3$. In this embodiment, the reaction byproducts $M^1Cl$ or $M^1Br$ are easily eliminated since they are insoluble in aprotic solvents.

In a 5th embodiment, an aluminum complex in which all the X groups are other than a $>CR_2R_3$ group is prepared in the presence of water starting from a soluble source of aluminum or aluminum hydroxide $Al(OH)_3$, with the pH being adjusted so as to ensure the formation of the Y—Al bond.

In general, the organic precursors of the boron or aluminum complexes, in particular triols, diol-monoacids, monoalcohol-diacids, and triacids in which one or more C=O groups are optionally replaced with a C=NCN, C=C(CN)₂ or C=S group, can be obtained by reactions within the scope of those skilled in the art, some of these precursors themselves being new compounds. For example, a $CR^2R^3$ group can be obtained in particular by means of an addition of aldol type. A $C(=O)R^9$ leaving group (in which $R^9$ is an OMe, OEt, $OCH_2CF_3$, $R^9COO$, $OC_6H_5$, $OC_6F_5$, $OC_6H_4NO_2$, Cl, Br, imidazolyl or hydroxysuccinimidyl group) can be replaced with a >NCN or >C(CN)₂ group, with optional protection of the other reactive groups of the target molecule. The general methods given here are those which make it possible to obtain the molecules most representative of the invention and showing the most varied range of their properties.

The ID complexes in which each of the three Y groups is O are hereinafter denoted ID-a complexes.

The precursor of a ID-a complex in which each of the 3 Y groups is O and each of the 3 X groups is $CR^2R^3$ and which corresponds to the formula

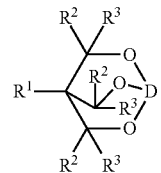

ID-a1 is a triol $R^1C[CR^2R^3OH]_3$.

When $R^1$ is a perfluorosulfonyl group, the triol $R_FSO_2C$—$[CHR^2OH]_3$ can be obtained by means of one of the following reactions:
- reaction of the potassium perfluoroalkane sulfonate $KR_FSO_2$ with a methylating agent, for example methyl toluenesulfonate $CH_3C_6H_4SO_3CH_3$;
- reaction of the sulfone $R_FSO_2CH_3$ with an aldehyde in the presence of a hindered strong base.

When $R^2$ is H, it is possible to use a source of formaldehyde such as paraformaldehyde, in the presence of 1,8-diazabicyclo[5.4.0]undec-7-ene (DBU) or of tetramethylguanidine as strong base. When $R^2$ is other than H, it is possible to use the corresponding aldehyde $R^2CHO$ with the same bases or a phosphorus-containing base of phosphazene type.

When $R^2$ and $R^3$ each represent H, the triol $R^1C(CH_2OH)_3$ is formed very readily in one step through the action of formaldehyde, acting as a hydroxymethylating and reducing agent on the aldehyde $RCH_2CHO$, according to the reaction:

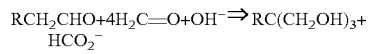

When $R^1$ is an electron-withdrawing group (for example, $NO_2$, CN, $CF_3CO$ or $CF_3SO_2$), the addition reaction takes place in the presence of basic catalysts, directly, without any oxidation-reduction reaction, according to the reaction scheme:

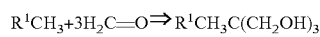

The same type of reaction takes place with the aldehydes $R^2CHO$ so as to give $R^1CH_3C(CHR^2OH)_3$.

A ID-a2 complex is a ID-a complex in which each of the 3 Ys is O, $X^1$ and $X^2$ each represent $CR^2R^3$ (in particular $CH_2$) and $X^3$ represents CO, and it is hereinafter denoted $R^1C\{[CR^2R^3O—]_2CO_2—\}B$.

The precursor of a ID-a2 complex is an $R^1C[CR^2R^3OH]_2$ $CO_2H$ compound which can react:
- with an alkyl borate in a polar protic solvent, for example a lower alcohol, or a polar aprotic solvent such as acetonitrile, so as to give a IB-a2 complex;
- with an aluminum alkoxide, an alkyl aluminum or a diaminoalkyl aluminum, so as to form a IAl-a2 aluminum complex, the alkoxides being preferred.

When $R^1$ is an alkyl group, the precursor $R^1C[CH_2OH]_2$ $CO_2H$ can be obtained by controlled oxidation, in particular enzymatic oxidation, of the corresponding triol $R^1C(CH_2OH)_3$.

When $R^1$ is H, the precursor $HC(CHR^2OH)_2COOH$ is obtained by condensation of the aldehyde $R^2CHO$ with a (methyl, ethyl) malonic ester, followed by decarboxylation.

A ID-a complex in which each of the 3 Ys is O, $X^1$ represents $CR^2R^3$ (in particular $CH_2$) and $X^2$ and $X^3$ each represent C=O, is hereinafter denoted ID-a3. The precursor of a ID-a3 complex is a compound $R^1C(CH_2OH)(CO_2H)_2$ which can react:
- with an alkyl borate or boric acid in a polar solvent, for example an alcohol containing from 1 to 4 carbon atoms, so as to form a boron complex;

with an aluminum alkoxide, an alkyl aluminum or a diaminoalkyl aluminum, so as to form a IAl-a3 aluminum complex, the alkoxides being preferred.

The precursor $R^1C(CH_2OH)(CO_2H)_2$ is obtained by condensation of one of the isomers of formaldehyde with the ester $R^1C(H)(CO_2Et)_2$ followed by hydrolysis of the ester functions to give $R^1C(CH_2OH)(CO_2H)_2$, at a moderate temperature so as to avoid decarboxylation.

A ID-a complex in which each of the Ys is 0, two $X^i$s represent $CR^2R^3$ (in particular $CH_2$), and one $X^i$ represents C=NCN is hereinafter denoted ID-a4. The precursor of a ID-a4 complex is a compound $R^1C(CH_2OH)_2[C(NCN)OM^1]$, $M^1$ being, for example, an alkali metal, which can react:

with a boron source such as an alkyl borate or boric acid, in the presence of an acid intended for releasing the —C(NCN)OH group, so as to form the IB-a4 complex;

with an aluminum alkoxide or aluminum hydroxide after addition of an acid capable of releasing —C(NCN)OH, so as to form the aluminum complex IAl-a4; or else with $AlCl_3$, $AlBr_3$, $AlF_3$ or $Al_2(SO_4)_3$ in the presence of two equivalents of a base Nu allowing the formation of the two bonds —$CR_1R_2O$—Al of the hydroxide of alcohol type by formation of $NuH^+X^-$, X representing one of the anions initially provided by the aluminum salt, so as to form a IAl-a4 aluminum complex.

The compound $R^1C(CH_2OH)_2[C(NCN)OM^1]$ can be obtained by means of a process comprising the following steps:

esterification of $R^1C(CH_2OH)_2(CO_2H)$ so as to obtain $R^1C(CH_2OH)_2(CO_2Me)$ or $R^1C(CH_2OH)_2(CO_2Et)$;

action of a salt $M^1HNCN$ for the formation of $R^1C(CH_2OH)_2[C(NCN)OM^1]$, M being, for example, an alkali metal.

A ID-a complex in which $X^1$ represents $CR^2R^3$ (in particular $CHR^2$ and $CH_2$) and $X^2$ and $X^3$ each represent C=NCN, is hereinafter denoted ID-a5.

The precursor of a ID-a5 complex is a compound corresponding to the formula $R^1C(CR^2HOH)[C(NCN)OM^1]_2$ which can be obtained by reacting $R^2CHO$ or HCHO with the malonic acid ester $R^1C(H)(CO_2Me)_2$ or $R^1C(H)(CO_2Et)_2$, followed by reacting two equivalents of a salt $M^1HNCN$ so as to give $R^1C(CR^2HOH)[C(NCN)OM^1]_2$, it being possible for $M^1$ to be an alkali metal.

The precursor $R^1C(CR^2HOH)[C(NCN)OM^1]_2$ can react with:

a boron source such as an alkyl borate or boric acid, in the presence of two equivalents of an acid intended for releasing the two C(NCN)OH groups, so as to form the complex IB-a5;

an aluminum alkoxide or aluminum hydroxide after addition of an acid capable of releasing —C(NCN)OH, so as to form the aluminum complex IAl-a5; or else $AlCl_3$, $AlBr_3$, $AlF_3$ or $Al_2(SO_4)_3$ in the presence of two equivalents of a base Nu allowing the formation of the two bonds —$CR_1R_2O$—Al of the hydroxide of alcohol type by formation of $NuH^+X^-$, X representing one of the anions initially provided by the aluminum salt, so as to form a IAl-a5 aluminum complex.

A ID-a complex in which each of the Y groups is O and each of the X groups represents a C=NCN group is hereinafter denoted ID-a6.

The precursor of a ID-a6 complex is a compound $R^1C[C(NCN)OM^1]_3$ which can be obtained by esterification of an alkali metal salt of a methanetricarboxylic acid triester $HC(CO_2Me)_3$ or $HC(CO_2Et)_3$, so as to give $R^1C(CO_2Me)_3$ or $R^1C(CO_2Et)_3$, followed by the action of at least three equivalents of a salt $M^1HNCN$.

The precursor $R^1C[C(NCN)OM^1]_3$ reacts with:

a boron source such as an alkyl borate or boric acid, in the presence of three equivalents of an acid, or through the action of a boron halide such as $BF_3$ or $BCl_3$, or through the action of boron triacetate $B(CH_3CO_2)_3$, so as to form the complex IB-a6;

an aluminum alkoxide or aluminum hydroxide after addition of an acid capable of releasing =C(NCN)OH, so as to form the aluminum complex IAl-a6; or else $AlCl_3$, $AlBr_3$, $AlF_3$ or $Al_2(SO_4)_3$, so as to obtain precipitation of the corresponding $M^1$ salts and the formation of the aluminum complex IAl-a6.

A ID-a complex in which each of the Y groups is O, two $X^i$ groups each represent a $CR^2R^3$ group and one $X^i$ group represents a C=C(CN)_2 group is hereinafter denoted ID-a7.

The precursor of a ID-a7 complex is a compound corresponding to the formula $R^1C(CH_2OH)_2[C[(C(CN)_2]OM^1]$ which can be obtained by esterification of $R^1C(CH_2OH)_2(CO_2H)$ so as to obtain $R^1C(CH_2OH)_2(CO_2Me)$ or $R^1C(CH_2OH)_2(CO_2Et)$, followed by the action of a salt $M^1HC(CN)_2$ derived from malononitrile.

The precursor $R^1C(CH_2OH)_2[C[(C(CN)_2]OM^1]$ can react with:

a boron source such as an alkyl borate or boric acid, in the presence of one equivalent of acid intended for releasing the —C[C(CN)_2]OH group, so as to form the complex IB-a7;

an aluminum alkoxide or aluminum hydroxide after addition of an acid capable of releasing —C(NCN)OH, so as to form the aluminum complex IAl-a7; or else $AlCl_3$, $AlBr_3$, $AlF_3$ or $Al_2(SO_4)_3$ in the presence of two equivalents of a base Nu allowing the formation of the two bonds —$CR_1R_2$—O—Al of the hydroxide of alcohol type by formation of $NuH^+X^-$, X representing one of the anions initially provided by the aluminum salt, so as to form a IAl-a7 aluminum complex.

A ID-a complex in which each of the Ys is 0, one $X^i$ group is a $CR^2H$ or $CH_2$ group and 2 $X^i$ groups are each a C=C(CN)_2 group is hereinafter denoted ID-a8.

The precursor of a ID-a8 complex is a compound $R^1C(CR^2HOH)$ $[\{C[(CN)_2OM^1]\}_2$ which can be obtained by reacting $R^2CHO$ (or HCHO) with the ester $R^1C(H)(CO_2Me)_2$ or $R^1C(H)(CO_2Et)_2$, and reacting two equivalents of a salt $M^1HC(CN)_2$, so as to give the salt $R^1C(CR^2HOH)[\{C[(CN)_2OM^1]\}_2$.

The precursor $R^1C(CR^2HOH)$ $[\{C[(CN)_2OM^1]\}_2$ can react with:

a boron source such as an alkyl borate or boric acid, in the presence of two equivalents of an acid intended for releasing the two —C[C(CN)_2OH] groups, so as to form the complex IB-a8, it being possible for the anion of the acid and the cation M to optionally be used to form an adduct of the invention;

an aluminum alkoxide or aluminum hydroxide after addition of an acid capable of releasing —C(NCN)OH, so as to form the aluminum complex IAl-a8; or else $AlCl_3$, $AlBr_3$, $AlF_3$ or $Al_2(SO_4)_3$ in the presence of two equivalents of a base Nu enabling the formation of the two bonds —$CR_1R_2$—O—Al of the hydroxide of alcohol type by formation of $NuH^+X^-$, X representing one of the anions initially provided by the aluminum salt, so as to form a IAl-a8 aluminum complex.

A ID-a complex in which each of the Ys is O and three X groups each represent a C=(CN)$_2$ group is hereinafter denoted ID-a9.

The precursor of a ID-a9 complex is a compound R$^1$C{[C[C(CN)$_2$OM$^1$]}$_3$ which can be obtained by esterification of an alkali metal salt of a methanetricarboxylic acid triester HC(CO$_2$Me)$_3$ or HC(CO$_2$Et)$_3$ so as to give R$^1$C(CO$_2$Me)$_3$ or R$^1$C(CO$_2$Et)$_3$, followed by the action of at least three equivalents of a salt M$^1$HC(CN)$_2$, so as to form the salt R$^1$C{[C[C(CN)$_2$OM$^1$]}$_3$.

The precursor R$^1$C {[C[C(CN)$_2$OM$^1$]}$_3$ can react with:
 a boron source such as an alkyl borate or boric acid, in the presence of three equivalents of an acid intended for releasing the three —C[C(CN)$_2$OH groups, so as to obtain the complex IB-a9, or else the latter can be obtained through the action of a boron halide such as BF$_3$ or BCl$_3$ or else boron triacetate B(CH$_3$CO$_2$)$_3$;
 an aluminum alkoxide or aluminum hydroxide after addition of an acid capable of releasing —C(NCN)OH, so as to form the aluminum complex IAl-a9; or else
 AlCl$_3$, AlBr$_3$, AlF$_3$ or Al$_2$(SO$_4$)$_3$, so as to obtain precipitation of the corresponding M$^1$ salts and formation of the aluminum complex IAl-a9.

Another family of complexes comprises the complexes, hereinafter denoted ID-b, in which each of the Y groups comprises a nitrogen atom, and the three X groups are CR$^2$R$^3$ groups, in particular the complexes in which each X group is a CH$_2$ group. These complexes correspond to the formula

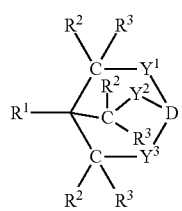

ID-b

The Y groups concerned are the following: >N(C=N), >N(COR$_F$), >N(SO$_2$R$^4$), >N(SO$_2$NR$^4_2$), >NR$^4$, >N(COR$^4$) and >N(SO$_2$R$_F$).

In general, an organic precursor having at least one Y group containing a nitrogen atom can be obtained from a compound which has either a ≡C—CN group or a —CR$^2$R$^3$(OH) group.

According to a first embodiment, the hydrogenation of a ≡C—CN group with hydrogen in the presence of a catalyst or with LiAlH$_4$ gives a —CH$_2$—NH$_2$ group. The resulting —CH$_2$NH$_2$ group can be modified with electrophilic sources of R"CO, R$_F$CO, R"SO$_2$, R$_F$SO$_2$, or CN groups which bond to the nitrogen atom of the amine group so as to give the ligands of the invention.

According to another embodiment, use is made of one of the precursors bearing at least one OH group mentioned for the preparation of certain ID-a complexes and the OH group of the —CR$^2$R$^3$(OH) group is replaced with a leaving group R$^{10}$ so as to give —CR$^2$R$^3$R$^{10}$(R$^{10}$ being chosen from Cl, Br, I, R$^{11}$SO$_3$, R$^3$R$^4$NSO$_3$ and R$_F$SO$_3$ (R$_F$, R$_3$, and R$_4$ being as defined above, R$^{11}$ being chosen from the groups defined above for R)), and then this is reacted with a nitrogenous nucleophilic compound, for example NH$_3$, or a salt of a nucleophilic anion such as, for example, C$_6$H$_4$(CO)$_2$N$^-$, (HCO)$_2$N$^-$, R"CONH$^-$, R$_F$CONH$^-$, R"SO$_2$NH$^-$ R$_F$SO$_2$NH$^-$, NCNH$^-$ and NCN$^{2-}$. The action of NH$_3$ gives an amine which can be treated in the same way as the amine obtained by hydrogenation of a nitrile group. The action of the salts of nucleophilic anions such as C$_6$H$_4$(CO)$_2$N— or (HCO)$_2$N$^-$ (Gabriel method) followed by hydrolysis releases the NH$_2$ group. The action of a salt of the other nucleophilic anions mentioned above directly gives the desired Y group.

A ID-b complex in which the three X groups each represent a CH$_2$ group and the 3 Y groups are each NCOCF$_3$ corresponds to the formula

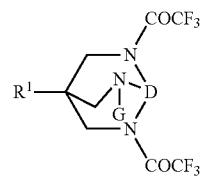

ID-b1 in which G is COCF$_3$.

The precursor of a ID-b1 complex is a compound of R$^1$C[CH$_2$N(H)COCF$_3$]$_3$ which can react with:
 an alkyl borate in a solvent such as an alcohol with a low number of carbon atoms, acetonitrile, acetone or THF, so as to give a IB-b1 complex;
 an aluminum alkoxide, an alkyl aluminum, a tris(dialkyl) aluminum or aluminum hydroxide, so as to form the aluminum complex IAl-b1; or else
 AlCl$_3$, AlBr$_3$, AlF$_3$ or Al$_2$(SO$_4$)$_3$ in the presence of three equivalents of a base Nu allowing the formation of the two bonds —CH$_2$—N(COCF$_3$)–Al, so as to form a IAl-b1 aluminum complex.

The precursor R$^1$C[CH$_2$N(H)COCF$_3$]$_3$ can be obtained by means of the following reactions:
 R$^1$C—(CH$_2$OH)$_3$+CH$_3$—C$_6$H$_4$—SO$_2$Cl⇒ =R$^1$C(CH$_2$OSO$_2$C$_6$H$_4$CH$_3$)$_3$ according to the method described by W. Stetter & H. Bockmann (*Chemische Berichte*, (1951), 84 834-9);
 reaction of LiH with CF$_3$CONH$_2$ in THF;
 after hydrogen has been given off, addition of CH$_3$C(CH$_2$OSO$_2$C$_6$H$_4$—CH$_3$)$_3$ at ambient temperature.

When R$^1$ is CH$_3$ or C$_2$H$_5$, the boron complexes correspond to the formulae

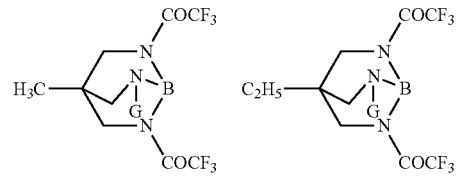

in which G is —COCF$_3$.

A compound ID-b1 in which R$^1$ is H is obtained from a precursor HC[CH$_2$NH(COCF$_3$)]$_3$ prepared by reacting the compound HC[CH$_2$NH$_2$]$_3$ with CF$_3$CO$_2$C$_2$H$_5$.

Said precursor can be brought into contact with
 an alkyl borate in an aprotic solvent so as to obtain a boron complex of the IB-b1 type;
 a source of aluminum so as to obtain an aluminum complex of the IAl-b1 type.

The triamine HC[CH$_2$NH$_2$]$_3$ can be obtained by reacting commercially available tricyanomethide K[C(CN)$_3$] with lithium aluminum hydride LiAlH$_4$, and then taking up in an aqueous solution of lithium hydroxide.

A ID-b complex in which the 3 Y groups are NCN, corresponding to the formula

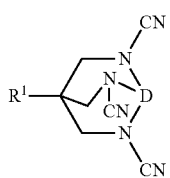

ID-b2 can be obtained from various organic precursors, by reacting a precursor with a source of boron so as to obtain a IB-b2 complex, or with a source of aluminum so as to obtain a IAl-b2 complex.

In a 1st embodiment, the organic precursor is prepared by reacting the triamine $R^1C(CH_2NH_2)_3$ (obtained by reduction of $R^1C(C\equiv N)_3$ as indicated above) with cyanoimidazole (three eq.).

In a 2nd embodiment, an organic precursor is prepared by reacting three equivalents of the nitrogenous nucleophilic compound $(M^1)^+[HNCN]^-$ (if $M^1$ is monovalent) or $(M^1)^{2+}[NCN]^{2-}$ (if $M^1$ is divalent) with the chloride $R^1C(CH_2Cl)_3$. The chloride is a commercially available product for $R^1=CH_3$. When $R^1 \neq CH_3$, the chloride $R^1C(CH_2Cl)_3$ can be obtained by treating the triol $R^1C(CH_2OH)_3$ with a chlorinating agent, for example $PCl_3$. In this 2nd embodiment, a bromide or an iodide can be used in place of the chloride. The bromides and the iodides are more reactive and they can be obtained by reacting $R^1C(CH_2OH)_3$ with a brominating or iodinating agent. The chloride substitution reaction is carried out in DMF or a light alcohol (MeOH or EtOH) at a medium temperature of the order of 65° C.

In a 3rd embodiment, a compound $R^1C(CH_2R^{12}SO_3)_3$ ($R^{12}$ being R, $R^3R^4N$, or $R_F$ with the meaning given above) is prepared through the action, on $R^1C(CH_2OH)_3$, of $R^{12}SO_3F$, $R^{12}SO_3Cl$ or $(R^{12}SO_2)_2O$ in the presence of a tertiary base, and then by reacting the compound obtained with $M^+[HNCN]^-$ (M=Li, Na, K, onium) or CaNCN so as to obtain the organic precursor.

A ID-b complex in which the 3 Y groups are $NSO_2R''$, corresponding to the formula

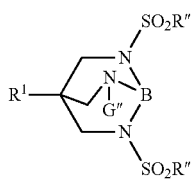

ID-b3 in which G" is $R''SO_2$ and R" is R, $R^3R^4N$ or $R_F$, can be obtained from various organic precursors, by reacting an organic precursor with a source of boron (for example, boric acid or an ester thereof) so as to obtain a IB-b3 complex, or with a source of aluminum so as to obtain a IAl-b3 complex.

According to a 1st embodiment, an organic precursor is prepared by reacting three equivalents of an electrophilic source $R''SO_2E$ (E being Cl, Im, $R''SO_3$) with the triamine $R^1C(CH_2NH_2)_3$ described above.

In a 2nd embodiment, an organic precursor is prepared by reacting the compound $R^1C(CH_2R^{14})_3$ in which $R^{14}$ represents Cl, Br, I or $R^ESO_3$ ($R^E$ preferably being $CH_3$, $CF_3$ or $CH_3C_6H_4$) with the nitrogenous anion (3 eq.) $R''SO_2NH^-$ in the form of an alkali metal salt or of an onium salt, according to the reaction

Another family of complexes comprises the complexes, hereinafter denoted ID-c, in which at least one Y group is O and at least one Y group comprises a nitrogen atom.

A ID-c complex in which one $Y^i$ group is O and 2 $Y^i$ groups are 2 $NCOCF_3$, corresponding to the formula

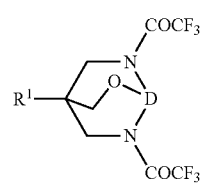

ID-c1

The precursor of a ID-c1 complex can be obtained by reacting the diamine $HOCH_2C(R^1)(CH_2NH_2)_2$ with ethyl trifluoroacetate, in acetonitrile, $R^1$ being alkyl.

The reaction of the precursor with a source of boron (or of aluminum) gives the complex IB-c1 (IAl-c1).

The diamine can be obtained by means of a process comprising the following steps:
  preparation of the alkylmalononitrile $R^1HC(CN)_2$ by means of the method published by J. Dunham, et al., [Synthesis, (2006), 680-686] by reacting sodium borohydride $NaBH_4$ with a mixture of an aldehyde $O=CHR^1$ and malononitrile;
  reaction of the alkylmalononitrile $R^1HC(CN)_2$ with an aldehyde $O=CHR^2$, catalyzed by a strong base such as DBU, so as to obtain $R^1C(CHR^2OH)(CN)_2$, $R^2$ having the definition given above;
  reaction of $R^1C(CHR^2OH)(CN)_2$ with $LiAlH_4$ so as to obtain the diamine $HOCH_2C(R^1)(CH_2NHR^2)_2$ or reduction with hydrogen.

A ID-c complex in which 2 $Y^i$ groups are each O and one $Y^i$ group is $NCOCF_3$, corresponding to the formula:

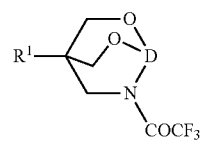

ID-c2 can be obtained from various organic precursors, which react with a source of boron [for example $B(OCH_3)_3$] or a source of aluminum.

In a first embodiment, the organic precursor is obtained by means of a process comprising the following steps:
  reaction of the tris(hydroxymethyl)alkane (of which two OH groups are protected, for example in carbonate form) with an agent replacing OH with a leaving group $R^{13}$ represents $Cl^-$, $Br^-$, $I^-$ or $R''SO_3$, and Gabriel reaction for example on the alkali metal salt of bis(formyl) imide,
  hydrolysis of the carbonate and of the formyl bonds so as to obtain the aminodiol,
  reaction with $CF_3COOC_2H_5$ so as to attach the trifluoroacetyl group to the amine.

In another embodiment, the aminodiol in which $R^1$ is H can be prepared by hydroxymethylation of methyl or ethyl cyanoacetate $NCC(CH_2OH)_2CO_2Me$ or $NCC(CH_2OH)_2CO_2Et$, followed by a hydrolysis-decarboxylation giving $HC(CH_2OH)_2(CN)$ and by reduction with hydrogen or $LiAlH_4$ so as to give $HC(CH_2OH)_2(CH_2NH_2)$.

A ID-c complex in which 2 $Y^i$ groups are each O and one $Y^i$ group is NCN, corresponding to the formula

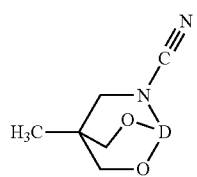

ID-c3 can be prepared from an organic precursor obtained by reaction of N-cyanoimidazole with the aminodiol described above for the preparation of the ID-c2 complex.

Said precursor is then brought into contact either with a source of boron [for example $B(OCH_3)_3$], or with a source of aluminum.

A ID-c complex in which 1 $Y^i$ group is O and two $Y^i$ groups each represent NCN, corresponding to the formula

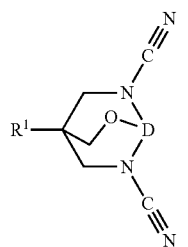

ID-c4 can be obtained from an organic precursor prepared by means of a process comprising the following steps:
  hydroxymethylation of an alkylmalononitrile $R^1HC(CN)_2$ with a source of methanal $H_2C=O$;
  reduction, with $H_2$ or $LiAlH_4$, of the hydroxymethylated monoalkyl malononitrile obtained, so as to obtain a diamino alcohol;
  reaction of the diamino alcohol with N-cyanoimidazole (2 equiv.), itself obtained in situ by reaction of CNBr with imidazole.

Said precursor is then brought into contact with a source of boron [for example one equivalent of $B(OCH_3)_3$] so as to obtain the boron complex, or with a source of aluminum.

Another subfamily of ID-c complexes comprises the complexes in which 2 $Y^i$ groups are each O and one $Y^i$ group is $NSO_2R''$, R'' being R, $R^3R^4N$ or $R_F$, corresponding to the formula

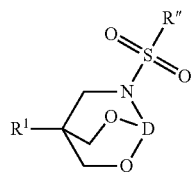

ID-c5

In a 1st embodiment, the organic precursor of a ID-c5 complex can be obtained by reaction of two equivalents of an electrophilic source $R''SO_2E$, E being a chloride, and an imidazoyl $C_3H_3N_2$— or $R''SO_3$—, with the aminodiol corresponding to the formula

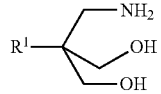

According to a 2nd embodiment, the organic precursor of a ID-c5 complex can be prepared by means of a process comprising the following steps:
  preparation of a compound $R^1C(CH_2OH)_2[CH_2R^{13}]$ in which $R^{13}$ represents Cl⁻, Br⁻, I⁻ or $R''SO_3$;
  reaction of the compound $R^1C(CH_2OH)_2[CH_2R^{13}]$ with a compound MJ in which J represents the anion $R''SO_2NH^-$, and M is an alkali metal cation or an onium cation, it being possible for said onium cation to be a cation obtained by bringing the amide $R''SO_2NH^2$ into contact with a tertiary base.

It may be preferable to protect the OH groups of $R^1C(CH_2OH)_2[CH_2R^{13}]$, with a conventional reactant, for instance hindered silanes, cyclic or noncyclic acetals, cyclic carbonates, tert-butoxycarbonate groups, and boronic acids.

A ID-c complex in which one $Y^1$ group is O and two $Y^i$ groups each represent $NSO_2R''$, in which R'' is R, $R^3R^4N$ or $R_F$, corresponding to the formula

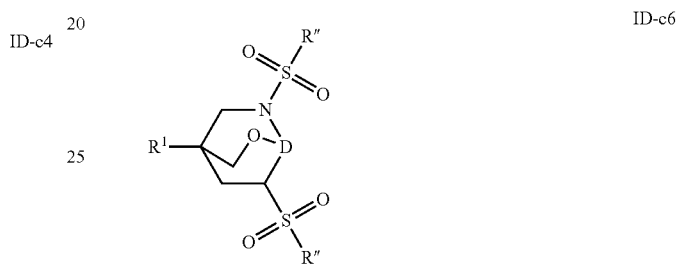

ID-c6 can be obtained from an organic precursor obtained by reacting the diamine monoalcohol $R^1H(CH_2OH)(CH_2NH_2)_2$ described above with the compound $R''SO_2E$ in which E is Cl, Im or $R''SO_3$.

The resulting compound is brought into contact with a source of boron, such as $B(OH)_3$ or esters thereof, or with a source of aluminum.

Precursors (denoted PTE) of II-D complexes can be obtained from triesters (TE) corresponding to the formula $R^1C(COOR^{14})_2(CR^2R^3—COOR^{15})$ in which Z is Cl, I or Br, and $R^{14}$ and $R^{15}$ are lower alkyl groups, which are preferably identical, more particularly a methyl or ethyl group. A triester TE can be obtained according to the following reaction scheme, in which Nu denotes a base:

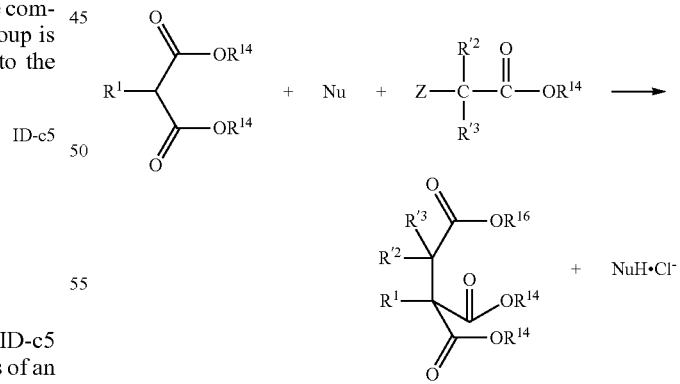

A TE compound makes it possible to prepare the precursors for various complexes in which the pairs $X^iY^i$ are identical. The IID complexes in which each of the Y groups is O are denoted IID-a. These PTE precursors are obtained by reacting a TE compound with a reactant $QHM^1$ in which $M^1$ is an alkali metal and Q is a group chosen from >O, >NCN and $C(CN)_2$. The general formula of the resulting PTE precursors is given in the table below:

| Q | Reactant | PTE |
|---|---|---|
| >O | M$^1$OH | R$^1$C(COOM$^1$)$_2$(CR$'^2$R$'^3$—COOM$^1$). |
| >NCN | M$^1$NH—CN | R$^1$C[C(NCN)OM$^1$]$_2$[CR$'^2$R$'^3$—C(NCN)OM$^1$]. |
| >C(CN)$_2$ | M$^1$HC(CN)$_2$ | R$^1$C{C[C(CN)$_2$]OM$^1$}$_2${CR$'^2$R$'^3$—C[C(CN)$_2$OM$^1$}. |

Other precursors (denoted PDL) of II-D complexes can be obtained from a monoalcohol diester (DL) R$^1$C(COOR$^{14}$)$_2$ (CR$'^2$R$'^3$—CR$^2$R$^3$OH), the two R$^{14}$ groups being identical lower alkyl groups, more particularly methyl or ethyl groups. The PDL precursors are also useful for preparing complexes of the IID-a type.

A DL compound can be prepared in the presence of a base Nu and a catalyst Cat according to the following reaction scheme, in the case where each of the R$^2$ and R$^3$ groups is H:

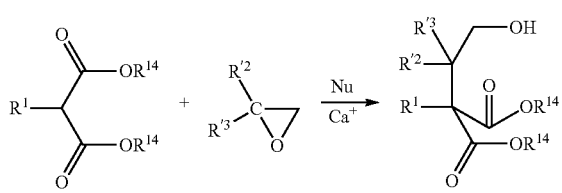

DL compounds in which at least one of the R$^2$ and R$^3$ groups is other than H can be obtained by replacing the oxirane with a suitable cyclic carbonate, in particular an ethylene carbonate or propylene carbonate.

A DL compound makes it possible to prepare the precursors for various complexes in which two pairs X$^i$Y$^i$ are identical. These precursors are obtained by reacting a DL compound with a reactant QHM in which M$^1$ is an alkali metal and Q is a group chosen from >O, >NCN and C(CN)$_2$. The general formula of the resulting PTE precursors is given in the table below:

| Q | Reactant | PTE |
|---|---|---|
| >O | M$^1$OH | R$^1$C(COOM$^1$)$_2$(CR$'^2$R$'^3$—CR$^2$R$^3$OH). |
| >NCN | M$^1$NH—CN | R$^1$C[C(NCN)OM"]2(CR$'^2$R$'^3$—CR$^2$R$^3$OH) |
| >C(CN)$_2$ | M$^1$HC(CN)$_2$ | R$^1$CC{C(CN)$_2$]OM"}$_2$(CR$'^2$R$'^3$—CR$^2$R$^3$OH) |

Other precursors (denoted PDM) of IID complexes can be obtained from a monoamine diacid (DM) R$^1$C(COOR$^{14}$)$_2$ (CR$'^2$R$'^3$-CR$^2$R$^3$NH$_2$), the two R$^{14}$ groups being identical lower alkyl groups, more particularly methyl or ethyl groups. A DM compound can be prepared in the presence of a base Nu according to the following reaction scheme, Z being I, Br or Cl, in the case where each of the R$^2$ and R$^3$ groups is H. DM compounds in which at least one of the R$^2$ and R$^3$ groups is other than H can be obtained by choosing a suitable amine halide of formula Z—CR$'^2$R$'^3$-CR$^2$R$^3$NH$_2$.

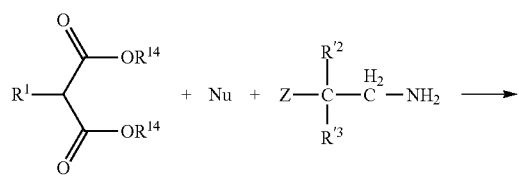

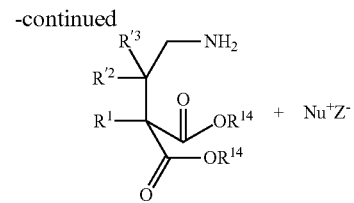

A DM compound makes it possible to prepare the precursors for various complexes in which two pairs X$^i$Y$^i$ are identical. These precursors are obtained by reacting a DM compound with a reactant QHM$^1$ in which M$^1$ is an alkali metal and Q is a group chosen from >O, >NCN and C(CN)$_2$. The general formula of the resulting PTE precursors is given in the table below. The IID complexes in which at least one of the Y groups is O and at least one of the Y groups comprises an N atom are denoted IID-c:

| Q | Reactant | PTE |
|---|---|---|
| >O | M$^1$OH | R$^1$C(COOM$^1$)$_2$(CR$'^2$R$'^3$—CR$^2$R$^3$NH$_2$). |
| >NCN | M$^1$NH—CN | R$^1$C[C(NCN)OM$^1$]$_2$[CR$'^2$R$'^3$—CR$^2$R$^3$OH] |
| >C(CN)$_2$ | M"HC(CN)$_2$ | R$^1$C{[C[C(CN)$_2$OM"]}2[CR$'^2$R$'^3$—CR$^2$R$^3$OH] |

In general, a precursor of a IIID complex can be obtained by coupling two molecules of the corresponding precursor of a ID complex. Likewise, a precursor of a IVD complex can be obtained by coupling two molecules of the corresponding precursor of a IID complex.

For example, a precursor of a IIID complex can be obtained according to the following reaction scheme:

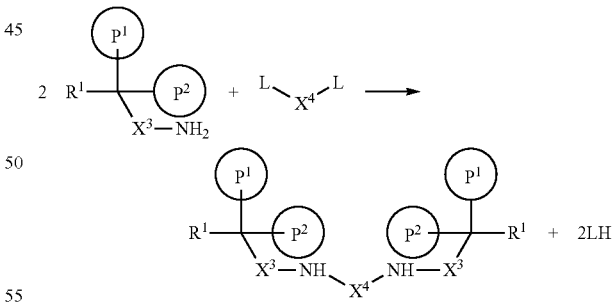

A precursor of a IIID complex can be obtained according to the following reaction scheme:

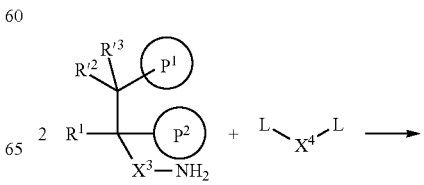

-continued

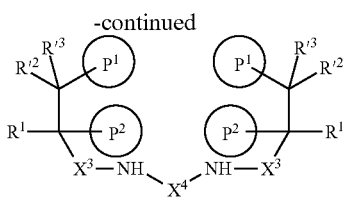

In the two reaction schemes above:

$X^4$ represents $>C=O$, $>C=NCN$ or $>C=C(CN)_2$, $>SO_2$ or $>C=S$;

L represents a leaving group, for example Cl, Br, or an imidazoyl, triazoyl or succinimidyl group. When L is Cl or Br, it is advantageous to add a base Nu so as to form $NuH^+Cl^-$ or $NuH^+Nu^-$ which is easy to eliminate;

$R'^2$, $R'^3$ and $X^3$ have the meaning given above;

$P^1$ and $P^2$ represent, respectively, a precursor group of the segment $X^1Y^1$ and $X^2Y^2$, for example in protonated form $X^1Y^1H$ and $X^2Y^2H$.

When $>X^1$ or $>X^2$ is $>O$, the corresponding group $P^1$ or $P^2$ can be $C(=O)OM''$, $C(=O)OCH_3$ or $C(=O)OC_5H_5$.

When $>X^1$ or $>X^2$ is $>C=NCN$, the corresponding group $P^1$ or $P^2$ can be $C(=NCN)OM''$, $C(=O)OCH_3$ or $C(=O)OC_5H_5$, (starting from which the change to NCN is made by reaction with $HNCN^-$), $C(=NCN)OCH_3$ or $C(=NCN)OC_5H_5$.

When $>X^1$ or $>X^2$ is $>N-C(CN)_2$, the corresponding group $P^1$ or $P^2$ can be $C[=C(CN)_2]OM''$, $C(=O)OCH_3$, $C(=O)OC_5H_5$ (starting from which the change to $C(CN)_2$ is made by reaction with $HC(CN)_2$), $C[=C(CN)_2]OCH_3$ or $C[=C(CN)_2]OC_5H_5$.

The IIID and IVD complexes in which $X^3$ is $CH_2$ can be prepared by means of an amidomethylation reaction, respectively according to the following reaction schemes:

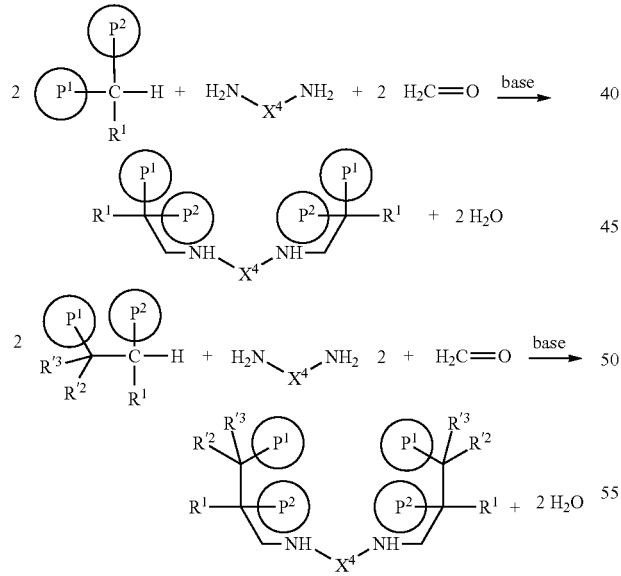

in which $R^1$, $R'^2$, $R'^3$, $P^1$, $P^2$ and $X^4$ have the meaning given above, $X^4$ being other than $>CR^2R^3$.

BRIEF DESCRIPTION OF THE DRAWINGS

FIG. 1 corresponds to the results obtained from solutions in the EC/DMC mixture and FIG. 2 to those obtained from solutions in DMF.

DETAILED DESCRIPTION

Figure 1:
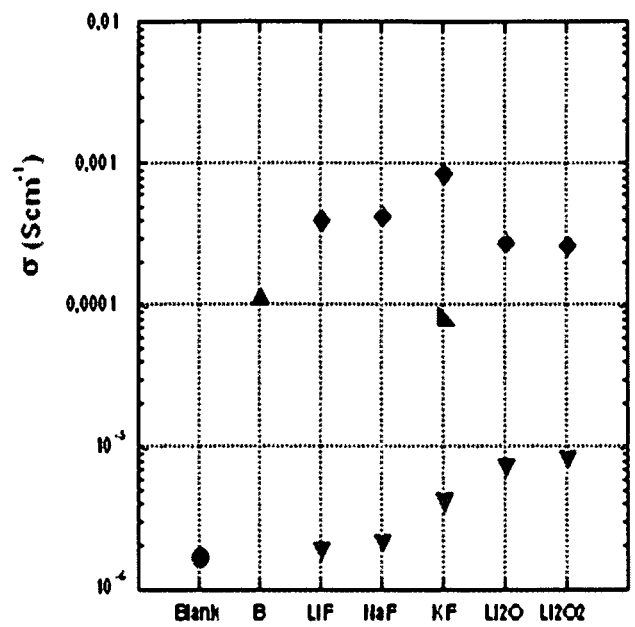
FIGS. 1 and 2 show measurements of conductivity at 25° C. carried out on the boron complex of example 1 and the adduct with KF of the aluminum complex of example 2, in, firstly, an ethyl carbonate/dimethyl carbonate (EC/DMC) mixture and, secondly, in dimethylformamide (DMF).

The present invention is illustrated by the following examples, to which it is not, however, limited.

Example 1

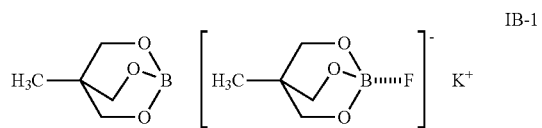

7.72 g of boric acid $B(OH)_3$ are added to 15 g of commercially available trimethylolethane $CH_3C(CH_2OH)_3$ and the mixture is dissolved in 60 ml of ethanol with magnetic stirring, with formation of the compound $CH_3C(CH_2O-)_3B$ (IB-1). 7.253 g of potassium fluoride are added. The fluoride is insoluble in ethanol, but dissolves rapidly in the presence of the $CH_3C(CH_2O-)_3B$ complex so as to form the adduct $[CH_3C(CH_2O-)_3BF]^-K^+$. The solvent is eliminated on a rotary evaporator, so as to give a white crystalline powder. The solubility of the adduct is 2.7 g.$L^{-1}$ in dimethylformamide (DMF).

Example 2

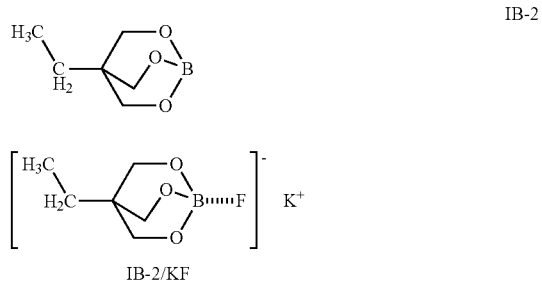

15.49 g of methyl borate $B(OCH_3)_3$ are added, in 75 ml of methanol, to 20 g of commercially available 2-ethyl-2-hydroxymethyl-1,3-propanediol (1,1,1-trimethylol-propane) $C_2H_5C(CH_2OH)_3$, with magnetic stirring. Substantial cooling is observed and the triol goes into solution. After the solvent has been evaporated off, the tricyclic complex $C_2H_5C(CH_2O-)_3B$ (IB-2) is obtained in the form of a white solid. 4.09 g of potassium fluoride are added to 10 g of this complex in 60 ml of absolute ethanol, and said potassium fluoride dissolves rapidly so as to form the adduct $K^+[C_2H_5C(CH_2O-)_3BF]^-$. The solvent is eliminated on a rotary evaporator, so as to give a white crystalline powder. The solubility of the IB-2/KF adduct is 17 g.$L^1$ in dimethylformamide (DMF).

Example 3

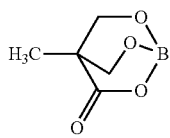

IB-3

13.061 g of ethyl borate B(OC$_2$H$_5$)$_3$ are added, in 75 ml of 95% ethanol, to 12 g of commercially available 2,2-bis(hydroxymethyl)propionic acid CH$_3$C(CH$_2$OH)$_2$CO$_2$H, with magnetic stirring. The clear solution obtained is evaporated under vacuum on a rotary evaporator and the drying is continued under a primary vacuum at 75° C. The syrupy mass is converted into a white solid which is isolated (quantitative yield) and corresponds to the formula CH$_3$C[(CH$_2$O—)$_2$(CO$_2$—)]B (IB-3). 6 g of this complex are dissolved in 25 ml of anhydrous dimethylformamide (DMF) and a clear solution is obtained. 2.46 g of potassium fluoride dried at 150° C. under a primary vacuum are added. KF, which is strictly insoluble in DMF, goes into solution rapidly so as to form the adduct K$^+${CH$_3$C[(CH$_2$O—)$_2$(CO$_2$—)BF}$^-$.

Example 4

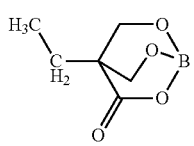

IB-4

10.52 g of methyl borate B(OCH$_3$)$_3$ are added, in 75 ml of methanol, to 15 g of commercially available 2,2-bis(hydroxymethyl)butyric acid C$_2$H$_5$C(CH$_2$OH)$_2$CO$_2$H, with magnetic stirring. The clear solution obtained is evaporated under vacuum on a rotary evaporator. The syrupy mass is converted into a white solid which is isolated with a quantitative yield and which corresponds to the formula C$_2$H$_5$C[(CH$_2$O—)$_2$(CO$_2$—)]B (IB-4). 8 g of this complex are dissolved in 25 ml of anhydrous dimethylformamide (DMF) and a clear solution is obtained. 2.98 g of potassium fluoride dried at 150° C. under a primary vacuum are added. A colorless clear solution of the adduct K$^+${C$_2$H$_5$C[(CH$_2$O—)$_2$(CO$_2$—)]BF}$^-$ is obtained.

Example 5

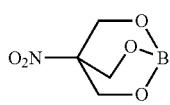

IB-5

20 g of commercially available tris(hydroxymethyl)nitromethane NO$_2$C(CH$_2$OH)$_3$ are added to a solution of 8.183 g of boric acid in 65 ml of methanol. The yellow solution is evaporated so as to leave a beige solid of formula NO$_2$C(CH$_2$O—)$_3$B (IB-5). 13.99 g of commercially available tetraethylammonium fluoride dihydrate (C$_2$H$_5$)$_4$NF·2H$_2$O are added to 12 g of this compound in 60 ml of methanol, as are 16 g of 2,2-dimethoxypropane CH$_3$C(OCH$_3$)$_2$CH$_3$ intended to react with the water formed. The clear yellow solution is evaporated so as to give an adduct in the form of an anhydrous solid (C$_2$H$_5$)$_4$N$^+$[NO$_2$C(CH$_2$O—)$_3$BF]$^-$. This salt is soluble in polar solvents, such as dichloromethane, acetonitrile, DMF, dimethylacetamide, DMSO, N-methylpyrrolidinone (NMP) or α,α,α-trifluorotoluene.

Example 6

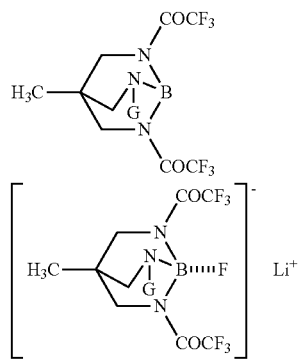

IB-6

IB-6/LiF with G = COCF$_3$

The sulfonic ester CH$_3$C(CH$_2$OSO$_2$C$_6$H$_4$CH$_3$)$_3$ is prepared according to the method of Stetter and Bockmann (W. Stetter & H. Bockmann, *Chemische Berichte*, (1951), 84 834-9) starting from trimethylolethane and toluenesulfonyl chloride in pyridine. 6.2 g of LiH are added to a solution of 44 g of trifluoroacetamide CF$_3$CONH$_2$ in 400 ml of tetrahydrofuran. After hydrogen has been given off, 75 g of the previously prepared sulfonic ester are added gradually to the suspension at normal temperature and with magnetic stirring. A further amount of hydrogen is given off. After two hours, the suspension is evaporated and the mixture is taken up with 500 ml of water to which 60 g of ammonium hydrogen sulfate have been added. The solution is extracted in ethyl ether in three portions of 300 ml. The combined extracts are evaporated and recrystallized from a toluene-acetonitrile mixture, so as to give 42 g of the complexing agent CH$_3$C(CH$_2$N(H)COCF$_3$)$_3$ (yield 80%). 8 g of the complexing agent are dissolved in 30 ml of methanol and 2.88 g of ethyl borate and 512 mg of LiF are added. The lithium fluoride dissolves in the form of the (IB-6/LiF) complex salt of formula {CH$_3$C[CH$_2$—N(COCF$_3$)—]$_3$BF}Li$^+$.

Example 7

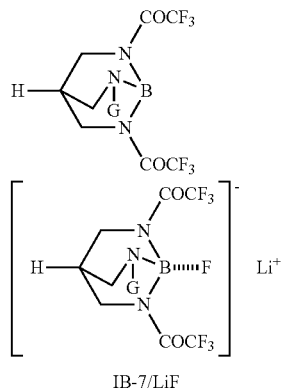

IB-7

IB-7/LiF 3 g of potassium tricyanomethide K[C(CN)$_3$] from a commercially available source were dissolved in 200 ml of THF, to which 12 g of lithium aluminum hydride LiAlH$_4$ were added. After two hours, the THF is eliminated with a rotary evaporator, the solid formed is taken up in 50 ml of water and 10 g of lithium hydroxide LiOH are added. The suspension is filtered and the water is evaporated off under reduced pressure. The pasty solid is extracted with 2 portions of 50 ml of dichloromethane $CH_2Cl_2$ and the solvent is evaporated off. The NMR analysis shows that the product obtained is the triamine $HC(CH_2NH_2)$ not disclosed in the prior art.

10 g of this amine, 41.4 g of ethyl trifluoroacetate $CF_3CO_2C_2H_5$, 14.2 g of triethyl borate and 2.52 g of LiF were introduced into 125 ml of acetonitrile. The clear solution confirms the formation of an adduct IB-7/LiF of the boron complex IB-7 of formula $HC[CH_2N(CF_3CO)—]_3B$ with LiF, despite the high reticular energy of said complex salt.

Example 8

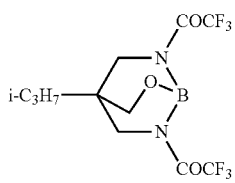

IB-8

Isopropylmalononitrile is prepared by the method of Dunham et al. (J. Dunham, A. Richardson, R. Sammelson, *Synthesis*, (2006), 680-686) by reacting 20 g of sodium borohydride $NaBH_4$ with a mixture of 60 ml g of acetone with 50 g of malononitrile in 200 ml of isopropanol and with stirring at 0° C. The solvent is evaporated off and the reaction mixture is taken up with 400 ml of water acidified with 50 g of sulfuric acid. The isopropylmalononitrile is extracted with 3 portions of 100 ml of ether. The fractions are combined and the ether is evaporated off. The isopropylmalononitrile is distilled at 85-86° C. at 7 mbar.

15 ml of a commercially available solution of formaldehyde at 37% in water and 10 drops of basic catalyst, 1,8-diazabicyclo[5.4.0]undec-7-ene (DBU) are added to 20 g of isopropylmalononitrile. A rapid reaction with heating gives $C_3H_7C(CH_2OH)(CN)_2$ (2-propyl-2-hydroxymethylmalononitrile) and the water is evaporated off under vacuum. The diamine $HOCH_2C(C_3H_7)(CH_2NH_2)_2$ (10 g) is obtained by reduction with lithium aluminum hydride $LiAlH_4$ (8 g) in THF (100 ml). After acidification and extraction with ether, the diamine is obtained by distillation after the addition of NaOH pellets.

To 4 g of the diamine are added, in acetonitrile, 7.7 g of ethyl trifluoroacetate and then 4 g of triethyl borate and 4.15 g of CsF. The resulting solution is evaporated and the adduct IB-8/CsF of formula i-$C_3H_7C\{[CH_2O—][CH_2—N(CO CF_3)_2—]\}BF^-Cs^+$ is obtained in the form of a white solid. This compound is soluble in polar aprotic solvents, unlike CsF.

Example 9

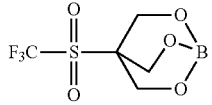

IB-9

20 g of potassium trifluoromethane sulfinate $KCF_3SO_2$ dissolved in 100 ml of acetonitrile are treated with 21.6 g of methyl toluenesulfonate $CH_3C_6H_4SO_3CH_3$ at 60° C. for 48 hours. The potassium toluenesulfonate precipitate is recovered by centrifugation and the solids are washed with two parts of 20 ml of acetonitrile. The resulting product is the sulfone $CF_3SO_2CH_3$ which is not isolated. The liquid phases are combined, and then 10.6 g of paraformaldehyde and 5 drops of DBU are added. The solution is stirred at ambient temperature and the insoluble paraformaldehyde gradually dissolves. The slightly cloudy suspension thus obtained is filtered and, after the acetonitrile has been evaporated off, the triol $CF_3SO_2C(CH_2OH)_3$ in the form of a white solid is recrystallized from a toluene-nitromethane mixture. 6.12 g of triethyl borate $B(OC_2H_5)_3$ are added to 10 g of this triol and a colorless solution in ethanol is obtained. Evaporation gives the complex $CF_3SO_2(CH_2O—)_3B$ (IB-9) in the form of a white powder.

The complex (IB-9) gives, with KF, KNCO, KCN and NaCN, adducts which are soluble in low-boiling-point polar solvents such as acetonitrile, acetone and ethyl methyl ketone, and, a fortiori, in more polar solvents such as DMF, DMSO, NMP and sulfolane.

Example 10

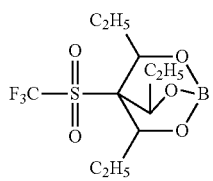

IB-10

15 g of propionaldehyde $C_2H_5CHO$ and 240 mg of phosphazene base $[CH_3)_2N]_3P=N—P(NC_2H_5)N(CH_3)_2]_2$ (marketed by the company Fluka under the reference 79417) are added to a solution of 20 g of trifluoromethylmethylsulfone $CF_3SO_2CH_3$ in 100 ml of acetonitrile. The reactor is hermetically closed and maintained at 20° C. in a water bath. After 24 hours, the solvent is eliminated by evaporation in a rotary evaporator, and a viscous oil $CF_3SO_2C[CH(C_2H_5)OH]_3$ is obtained. 4.83 g of trimethyl borate $B(OCH_3)_3$ were added to 15 g of this compound. The reaction scheme is the following:
$CF_3SO_2C[CH(C_2H_5)OH]_3+B(OCH_3)_3 \Rightarrow 3CH_3OH+ CF_3SO_2C[CH(C_2H_5)O—]_3B$.

The IB-11 complex is obtained in the form of a clear solution in methanol which forms simultaneously. The complex is recovered by evaporating off the methanol.

Example 11

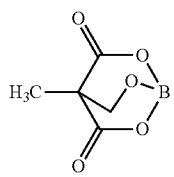

IB-11

8.2 ml of a commercially available solution of formaldehyde at 37% in water, 10 ml of 95% ethanol and 8 drops of DBU, as basic catalyst, are added to 17.4 g of the commercially available diethyl ester of methylmalonic acid $CH_3CH(CO_2C_2H_5)_2$. Starting from the two immiscible phases, a rapid reaction with heating gives ethyl 2-methyl-2-hydroxymethylmalonate $CH_3C(CH_2OH)(CO_2C_2H_5)_2$. The colorless single-phase solution obtained is diluted with 60 ml of 95% ethanol and 10 ml of water. 8 g of $Ca(OH)_2$ are dispersed and the mixture is stirred for 72 hours at 35° C. 2.5 g of acetic acid are added to the resulting white suspension, in order to eliminate the excess Ca(OH)$_2$. The insoluble calcium salt resulting from the saponification is separated by filtration, washed with 95% ethanol and dried. Its formula corresponds to Ca[CH$_3$C(CH$_2$OH)(CO$_2$)$_2$]. 8 g of the calcium salt and 3.5 g of anhydrous oxalic acid are dispersed, with magnetic stirring, in 50 ml of anhydrous ethanol. After two hours, the white suspension obtained is centrifuged and the solid is exhausted with 3×12 ml of ethanol. The fractions are combined and 5.6 g of ethyl borate B(OC$_2$H$_5$)$_3$ are added. After the solvent has been evaporated off, the diacid-alcohol boron complex CH$_3$C[(CH$_2$O—)(CO$_2$—)$_2$]B (IB-11) is obtained.

Example 12

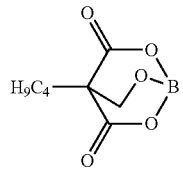

IB-12

3.1 g of paraformaldehyde and 20 drops of DBU are added to 21.6 g of the commercially available diethyl ester of butylmalonic acid C$_4$H$_9$CH(CO$_2$C$_2$H$_5$)$_2$. A gradual reaction, shown by the disappearance of the suspension of paraformaldehyde, gives ethyl 2-butyl-2-hydroxymethylmalonate C$_4$H$_9$C(CH$_2$OH)(CO$_2$C$_2$H$_5$)$_2$ in the form of a colorless liquid, which is subsequently diluted with 70 ml of 95% ethanol and 10 ml of water. 8 g of calcium hydroxide Ca(OH)$_2$ are dispersed and the mixture is stirred for 72 hours at 35° C. 4 g of acetic acid are added to the white suspension obtained and the calcium salt precipitate which is formed is separated by filtration, washed with 95% ethanol and dried. Its formula corresponds to Ca[C$_4$H$_9$C(CH$_2$OH)(CO$_2$)$_2$].

10 g of this calcium salt and 3.8 g of anhydrous oxalic acid are dispersed, with magnetic stirring, in 60 ml of anhydrous ethanol. After two hours, the white suspension formed is centrifuged and the solid is exhausted with 3×12 ml of ethanol. The fractions are combined and 4.35 g of methyl borate B(OCH$_3$)$_3$ are added. After the solvent has been evaporated off, the diacid-alcohol boron complex C$_4$H$_9$C[(CH$_2$O—)(CO$_2$—)$_2$]B (IB-12) is obtained in the form of a colorless solid.

Example 13

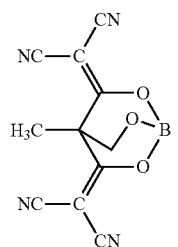

IB-13

13.8 g of malononitrile and 11 g of sodium methoxide were added, under argon and in a glovebox, to 20.4 g of diethyl (2-methyl-2-hydroxymethylmalonate) of formula CH$_3$C(CH$_2$OH)(CO$_2$C$_2$H$_5$)$_2$ prepared according to example 11 in 100 ml of DMF. The solution was stirred in a glovebox and a white precipitate formed. The stirring was maintained for 24 hours and the precipitate was separated by centrifugation, and washed with two portions of acetonitrile. After drying, the dibasic salt Na$_2${CH$_3$C(CH$_2$OH)[COC(CN)$_2$]$_2$} was isolated. 10 g of salt, 3.28 g of boron trifluoride etherate and 1.69 g of triethyl borate were mixed in 50 ml of acetonitrile. The following reaction occurs:

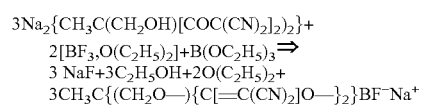

The adduct of NaF and of the IB-13 boron complex is soluble in polar aprotic solvents such as acetonitrile, THF, glymes, DMF, NMP and sulfolane and solvating polymers such as poly(ethylene oxide) and copolymers thereof.

The lithium salt can be obtained either by replacing CH$_3$ONa during the synthesis with the same molecular amount of lithium alkoxide or of LiH, or by ion exchange using LiCl which precipitates NaCl in any of the solvents mentioned above in which NaCl is insoluble. In the same way, an onium salt as defined above can be obtained by reaction of the appropriate onium chloride. A salt of a heavier alkali metal (K, Rb, Cs) is obtained by reacting the corresponding metal fluoride, with concomitant precipitation of NaF.

The replacement of diethyl (2-methyl-2-hydroxymethylmalonate) with diethyl (2-butyl-2-hydroxymethylmalonate) gives C$_4$H$_9$C{(CH$_2$O—){C[=C(CN)$_2$]O—}$_2$}BF$^-$Na$^+$ which can subsequently be subjected to various cation exchange reactions.

Example 14

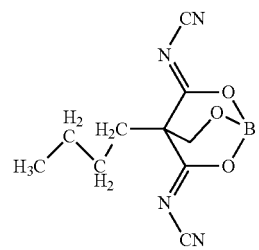

IB-14

13 g of commercially available NaHNCN were added to 24.6 g of C$_4$H$_9$C(CH$_2$OH)(CO$_2$C$_2$H$_5$)$_2$ prepared as in example 12 in 150 ml of absolute ethanol. The solution was heated to 50° C. and was maintained at this temperature with stirring for 24 hours. The precipitate formed was centrifuged, and then washed with two parts of absolute ethanol. After drying, the dibasic salt Na$_2$[C$_4$H$_9$C(CH$_2$OH)(CONCN)$_2$] is obtained in the form of a white powder.

11.75 g of this salt was suspended in 100 ml of acetonitrile, the suspension was cooled to 0° C., and a solution of 2.08 g of H$_2$SO$_4$ at 98% in 20 ml of 1,4-dioxane was added dropwise. The suspension was filtered in order to eliminate the sodium sulfate formed. The residue was washed with two portions of acetonitrile, and 6.08 g of B(OC$_2$H$_5$)$_3$ were added to the filtrate. The solvent was eliminated on a rotary evaporator and the residual colorless solid was dried under a primary vacuum at 50° C. 9.38 g of a boron complex of formula C$_4$H$_9$C{[CH$_2$O—][C(=NCN)—O—]$_2$}B (IB-14) were obtained (yield 94%).

The complex CH$_3$C{[CH$_2$O—][C(=NCN)—O—]$_2$} IB-14″ is obtained by replacing C$_4$H$_9$C(CH$_2$OH)(CO$_2$C$_2$H$_5$)$_2$ with 20.4 g of CH$_3$C(CH$_2$OH)(CO$_2$C$_2$H$_5$)$_2$.

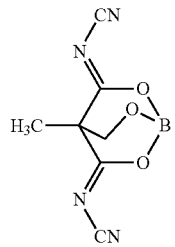

IB-14″

The boron complex obtained forms adducts with alkali metal fluorides or onium fluorides, and also with Li$_2$O$_2$, LiOCN, NaOCN, NaCN, KCN and NaN$_3$. For example, 2.04 g of IB-14 complex and 280 mg of LiF are dispersed in acetonitrile. The majority of the LiF dissolves. The slightly cloudy solution is centrifuged, the residue is subjected to evaporation, and 2.05 g (yield of 89%) of the adduct Li{CH$_3$C(CH$_2$O—)[C(=NCN) O—]$_2$BF} IB-14/LiF are obtained.

Example 15

26 g of commercially available carbonyldiimidazole CO(C$_3$H$_3$N$_2$)$_2$ are added to 20 g of commercially available trimethylolethane CH$_3$C(CH$_2$OH)$_3$ in 85 ml of THF. The mixture is stirred at normal temperature, and then 35 g of sulfamic acid are added and the mixture is again stirred for 24 hours and filtered. The compound obtained is the triol of which two functions are protected by formation of a cyclic carbonate.

The filtrate is treated with 31.5 g of toluenesulfonyl chloride and 12.6 g of pyridine. The reaction product is filtered in order to eliminate the pyridinium chloride precipitate. The filtrate is evaporated and taken up in DMF and 15.8 g of the sodium salt of bisformylimide (HCO)$_2$NNa are added. The solution is maintained at 80° C. with stirring for 2 hours. After cooling, the mixture is diluted in 300 ml of water and the solution is extracted with three portions of 50 ml of ethyl ether and the extracts are combined. After evaporation, 24.1 g (72%) of the compound CH$_3$C{[(CH$_2$O)$_2$]CO}CH$_2$N(CHO)$_2$ are obtained.

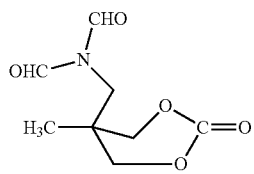

15 g of this compound are solubilized in 150 ml of water, and 11 g of calcium hydroxide are added. The solution is brought to reflux for 3 hours. The white suspension which forms is filtered, and the water is evaporated off. The solid is extracted with 50 ml of dichloromethane and the solvent is eliminated. 7.7 g (84%) of CH$_3$C(CH$_2$OH)$_2$CH$_2$NH$_2$ are obtained in the form of a viscous liquid. This amino alcohol was used as a precursor for the formation of boron complexes according to the invention, in acetonitrile, at normal temperature. When the reactant is (CH$_3$)$_2$NSO$_2$Cl, one equivalent of DABCO (diaza-1,4-bicyclo[2.2.2]octane) base is added.

The following table gives examples of compounds of the invention obtained from this precursor.

| Precursor | | | | |
|---|---|---|---|---|
| | H$_3$C—C(—NH$_2$)(—OH)(—OH) | | | |
| Reactant | CF$_3$COOC$_2$H$_5$ | F$_3$C—S(O)$_2$—N(imidazole) | (CH$_3$)$_2$NSO$_2$Cl | N≡C—N(imidazole) |
| Boron source | B(OCH$_3$)$_3$ | B(OH)$_3$ | B(OC$_2$H$_5$)$_3$ | B(OCH$_3$)$_3$ |
| Boron complex | 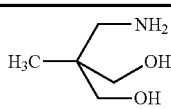 IB-15a | 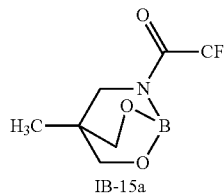 IB-15b | 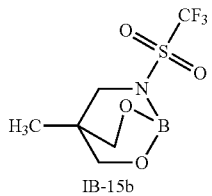 IB-15c | 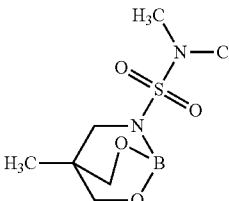 IB-15d |

The 4 boron complexes thus prepared form adducts with the fluorides of alkali metals having a size at least equal to that of K$^+$, i.e. Rb and Cs, and with all the fluorides of onium salts.

Example 16

Butylmalononitrile was prepared from butanal and malononitrile according to the process described by Dunham et al. (*Synthesis*, (2006), 680-686). 3.0 g of paraformaldehyde and 8 drops of DBU were added to 12.2 g of butylmalononitrile in 100 ml of TI-IF. The paraformaldehyde gradually disappears, as it reacts so as to hydroxymethylate the malononitrile and give the compound C$_4$H$_9$C(CH$_2$OH)(CN)$_2$. 11 g of LiAlH$_4$ are added to the solution obtained, with stirring. After two hours, the THF is eliminated on a rotary evaporator. The dry solid is taken up by adding 100 ml of water, dropwise for the first 10 ml, and 5 g of LiOH are added. The solvent is again eliminated, and the pasty solid is extracted with 2 portions of 50 ml of α,α,α,-trifluorotoluene and the solvent is eliminated by distillation. The NMR analysis shows that the compound obtained is the diamino alcohol C$_4$H$_9$C(CH$_2$NH$_2$)$_2$(CH$_2$OH). It was used with various reactants in acetonitrile, at normal temperature, to prepare complexes according to the invention. When the reactant is C$_2$H$_5$SO$_2$Cl, one equivalent of DABCO (diaza-1,4-bicyclo[2.2.2]octane) base is added.

evaporated off so as to leave the ethyl ester of bis(hydroxymethyl)butyric acid C$_2$H$_5$C(CH$_2$OH)$_2$CO$_2$C$_2$H$_5$.

Carrying out the process in a glovebox under an argon atmosphere, 6.5 g of malononitrile and 5 g of sodium methoxide are dissolved in 50 ml of anhydrous THF and 16 g of the previously formed ester are added. After stirring for 24 hours, 2 ml of acetic acid are added and then the solution is removed from the glovebox, and the solvent is evaporated off. The residue is washed with dichloromethane and then extracted with acetonitrile (ACN) in which the salt formed is soluble. The solution is filtered in order to eliminate the sodium acetate which is insoluble in ACN, and then evaporated under

| Precursor | | 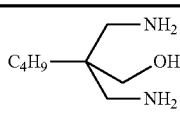 | | |
|---|---|---|---|---|
| Reactant (× 2): | CF$_3$COOC$_2$H$_5$ | 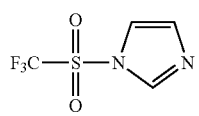 | C$_2$H$_5$SO$_2$Cl | 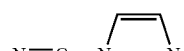 |
| Boron source | B(OC$_2$H$_5$)$_3$ | B(OCH$_3$)$_3$ | B(OH)$_3$ | B(OCH$_3$)$_3$ |
| Product obtained | 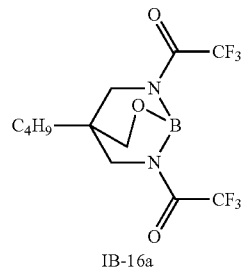<br>IB-16a | 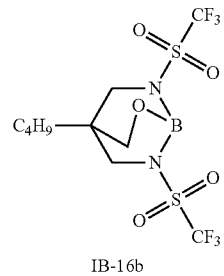<br>IB-16b | 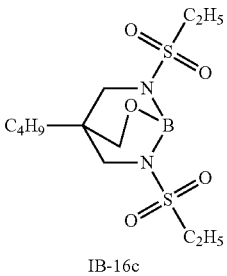<br>IB-16c | 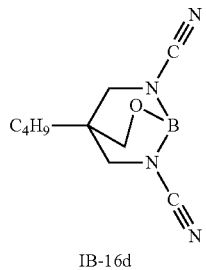<br>IB-16d |

Example 17

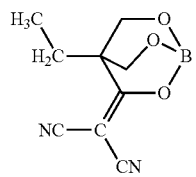

IB-17

25 g of commercially available bis(hydroxymethyl)butyric acid are dissolved in 150 ml of a 20/80 v/v mixture of water and ethanol, and 14.2 g of sodium hydrogen carbonate are added with stirring. Once no more CO$_2$ is being given off, the solution is filtered and the salt is evaporated under reduced pressure. The Na[C$_2$H$_5$C(CH$_2$OH)$_2$CO$_2$] salt is recovered in the form of a white solid. 17 g of this salt are suspended in 80 ml of methanol and 15 g of ethyl sulfate are added. After stirring for two hours at 25° C., the solution is evaporated and the pasty solid is extracted with 2×50 ml of dichloromethane and the extracts are combined. After filtration, the solvent is reduced pressure so as to give the Na[C$_2$H$_5$C(CH$_2$OH)$_2$COC(CN)$_2$] salt which is recrystallized from an acetonitrile/toluene mixture.

A complex of boron and of NaF is formed by reacting 10 g of salt previously prepared in 50 ml of ethanol, 2.834 g of boric acid B(OH)$_3$ and 2.9 g of a solution of hydrofluoric acid at 40% in water, in a polypropylene beaker. The solution obtained is evaporated so as to give the adduct of the IB-17 complex and of NaF.

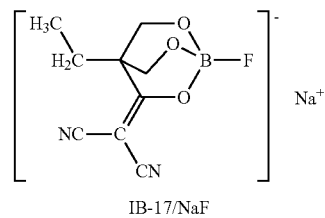

IB-17/NaF

This salt is soluble in polar solvents such as DMF, NMP, DMSO, acetonitrile, THF, 1,2-dimethoxyethane (glyme), diglyme or triglyme, whereas NaF is insoluble in all aprotic solvents. Through the action of KF and cation exchange in acetonitrile, the potassium salt is obtained, which is also soluble in solvents such as acetonitrile, THF or glymes.

Example 18

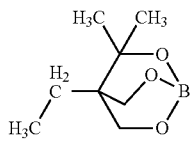
IB-18

17.6 g of the ethyl ester of bis(hydroxymethyl)butyric acid $C_2H_5C(CH_2OH)_2CO_2C_2H_5$, prepared in example 17, are dissolved in 100 ml of THF and 160 ml of a 2 M commercially available solution of methylmagnesium chloride in THF are added with mechanical stirring. A development of gas ($CH_4$) occurs and a white precipitate is formed. After 24 hours, 25 g of fine sulfamic acid powder are added and the stirring is continued for 48 hours. The reaction mixture is filtered and the THF is evaporated off so as to leave a viscous liquid of the triol $C_2H_5C(CH_2OH)_2[C(CH_3)_2OH]$ which is purified by chromatography. 3.81 g of boric acid $B(OH)_3$ are added to 10 g of this triol in 50 ml of acetonitrile. The light solution obtained is evaporated so as to obtain a colorless solid corresponding to the structure:

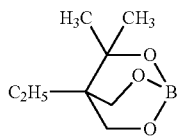

4.97 g of this complex are dissolved in 40 ml of DMF and 1.70 g of potassium fluoride KF are added. The salt rapidly goes into solution so as to give the complex $K^+\{C_2H_5C(CH_2O-)_2[C(CH_3)_2O-]BF\}^-$. The solution is added to 2.5 g of poly(epichlorohydrin) (commercially available polymer, Mw≈106) in 50 ml of DMF and the mixture is brought to 85° C. A KCl precipitate forms after 2 hours and the reaction is continued for 24 hours. The reaction mixture is poured into 100 ml of water and the polymer precipitated is filtered off and washed with water. The elemental analysis shows that 86% of the chlorine atoms of the polymer were substituted with fluorine atoms without chain degradation. The absence of vinyl ether bonds originating from the elimination of HCl is verified by IR. The same attempt at substitution with KF in DMF at 85° C. gives 100% elimination.

Example 19

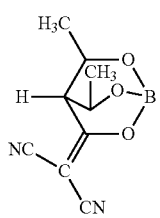
IB-19

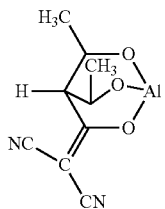
IA1-19

8.8 g of acetaldehyde $CH_3CHO$ were added to a solution of 50 ml of anhydrous methanol containing 13.2 g of dimethyl malonate $CH_2(CO_2CH_3)_2$ and 0.4 g of sodium methoxide, thermostatted at 5° C. with stirring, and then the mixture was left to react for one hour. 4 g of NaOH were then added to this solution, and then the mixture was maintained at 30° C. with stirring for two hours. Next, 9.71 g of sulfamic acid $HSO_3NH_2$ were added and the stirring was maintained at 30° C. for one hour. After filtration in order to eliminate $NaSO_3NH_2$ formed, the solution was brought to boiling, with $CO_2$ being given off. The solution containing the diol ester $HC[CH(CH_3)OH]_2CO_2CH_3$ thus obtained is degassed with nitrogen, and, under an inert atmosphere, 3.3 g of malononitrile and 2.7 g of sodium methoxide are added. The solution is stirred for 12 hours under a nitrogen atmosphere. 3 ml of acetic acid are subsequently added and then the methanol is evaporated off and the residual solution is extracted with 50 ml of acetonitrile, and then filtered.

The extract is precipitated from 100 ml of dichloromethane and 9.6 g of $Na\{HC[CH(CH_3)OH]_2COC(CN)_2\}$ are obtained in the form of a white powder.

The following are mixed: 7.27 g of $Na\{HC[CH(CH_3)OH]_2COC(CN)_2\}$, 3.24 g of sulfamic acid $HSO_3NH_2$ and 2.06 g of boric acid, in a 50/50 by volume ethanol/acetonitrile mixture, and then the solvent is evaporated off. The IB-19 complex is obtained.

In a 2nd trial, the following are mixed: 2.06 g of boric acid and 7.27 g of $Na\{HC[CH(CH_3)OH]_2COC(CN)_2\}$, in methanol, and then the methanol is eliminated, and the IB-19/NaOH adduct formed by the IB-19 complex with the $OH^-$ anion is obtained.

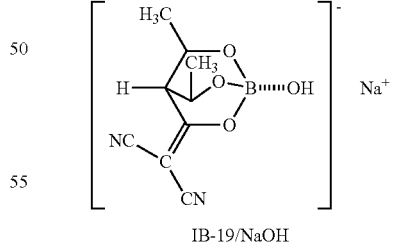
IB-19/NaOH

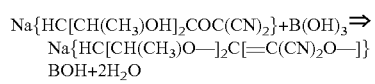

In a 3rd trial, 7.27 g of $Na\{HC[CH(CH_3)OH]_2COC(CN)_2\}$ and 1.67 g of a commercially available 40% solution of HF are added to water, and the adduct formed by the complex with the $F^-$ anion is obtained.

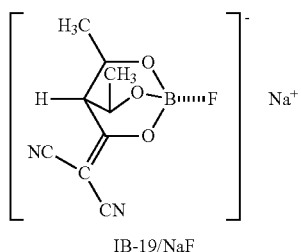

IB-19/NaF

In a 4th trial, 7.27 g of Na{HC[CH(CH$_3$)OH]$_2$COC(CN)$_2$}, 6.8 g of aluminum tris(isopropoxide) and 1.64 g of commercially available 98% sulfuric acid are added to ethanol, while cooling to 10° C. The mixture is then filtered so as to eliminate Na$_2$SO$_4$ formed, and the IAl-19 aluminum complex is obtained.

In a 5th trial, 7.27 g of Na{HC[CH(CH$_3$)OH]$_2$COC(CN)$_2$}, 8.21 g of aluminum tris(tert-butoxide) and 5 g of a commercially available 40% solution of HF are mixed in water, the mixture is filtered in order to eliminate NaHF$_2$ formed, and a solution of the IAl-19/NaF adduct is obtained.

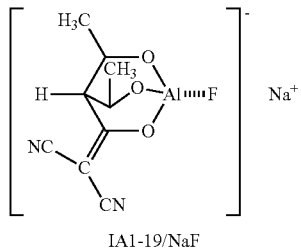

IA1-19/NaF

Example 20

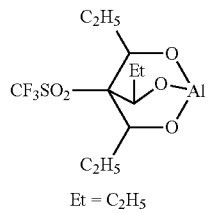

Et = C$_2$H$_5$ 11 g of the triol CF$_3$SO$_2$C[CH(C$_2$H$_5$)OH]$_3$ (obtained by condensing propanal with the sulfone CF$_3$SO$_3$CH$_3$ in the presence of a basic catalyst such as DBN (1,5-diazabicyclo[4.3.0]non-5-ene), the process being carried out in a glovebox), were dissolved in 60 ml of dry DMF, and 6.97 g of aluminum isopropoxide [CCH$_3$)$_2$CHO]$_3$Al were added. 2.1 g of dry KF was added to the clear solution obtained, said dry KF dissolving virtually completely so as to form the adduct in solution K$^+${CF$_3$SO$_2$C[CH(C$_2$H$_5$)O]$_3$AlF$^-$}. The excess KF was eliminated by centrifugation.

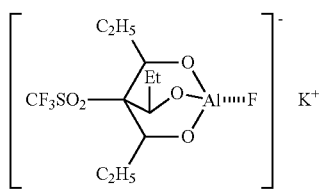

1.52 g of cesium fluoride were added, under the same conditions, to 6.45 g of the same triol and 4.08 g of aluminum isopropoxide. The salt goes into solution. The $^{19}$F and $^{27}$Al NMR indicates the formation of a trinuclear complex:

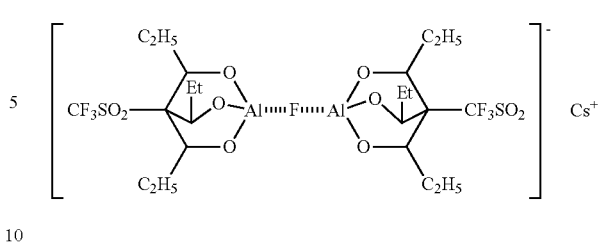

Example 21

14.6 g of butanal C$_3$H$_7$CHO were added to a solution containing 16 g of diethyl malonate CH$_2$(CO$_2$C$_2$H$_5$)$_2$ and 5 drops of diazabicyclo[5.4.0]undec-7-ene in 75 ml of acetonitrile, thermostatted at 10° C. with stirring, and then the mixture was left to react for 2 hours. The acetonitrile was subsequently eliminated under vacuum and 50 ml of water and 8.4 g of lithium hydroxide monohydrate were added to the clear viscous solution. The solution was kept at 40° C. for 3 hours, and then 6 g of sulfuric acid were added and the mixture was rapidly brought to boiling, which caused gas (CO$_2$) to be visibly given off. The solution was evaporated to dryness, and the diol monoacid HC[CH(C$_3$H$_7$)OH]$_2$CO$_2$H obtained was extracted with 2×50 ml of dichloromethane.

50 ml of triisobutyl aluminum [(CH$_3$)$_2$CHCH$_2$]$_3$Al, 1 M in THF, were added, with stirring in a glovebox, to 10.2 g of this acid in 60 ml of diethylene glycol dimethyl ether (diglyme, DG). Gas (isobutane) was violently given off, and a clear solution was obtained. 4.055 g of KOCN was added to this solution, and said KOCN went into solution, forming an adduct with the complex.

In another trial, 2.9 g of KF were added, and also dissolved, forming an adduct with the complex. The formula of the complex and of the two adducts is given below.

IA1-21

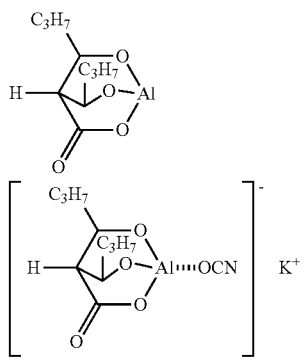

IA1-21/KOCN

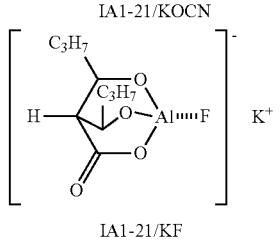

IA1-21/KF

Example 22

A commercially available ethyl cyanoacetate (a) was reacted with paraformaldehyde in the presence of 1% of diazabicyclo[5.4.0]undec-7-ene, and the compound (b) NCC(CH$_2$OH)$_2$CO$_2$C$_2$H$_5$ was obtained. This ethyl ester was hydrolyzed in a basic medium, and then, after release of the acid form, decarboxylation and protection of the OH groups with carbonyldiimidazole CO(C$_3$H$_3$N$_2$)$_2$, the compound (d) was obtained.

N,N'-biscyanoamidine is then prepared according to the process described in CS-273050-B1, by reacting (d) with HCl in ethanol so as to obtain the ethylamidate group of the compound (e), which is converted to a dicyanoamidine group —C(NCN)$_2$— in the compound (f).

The reaction scheme for the entire process is given below.

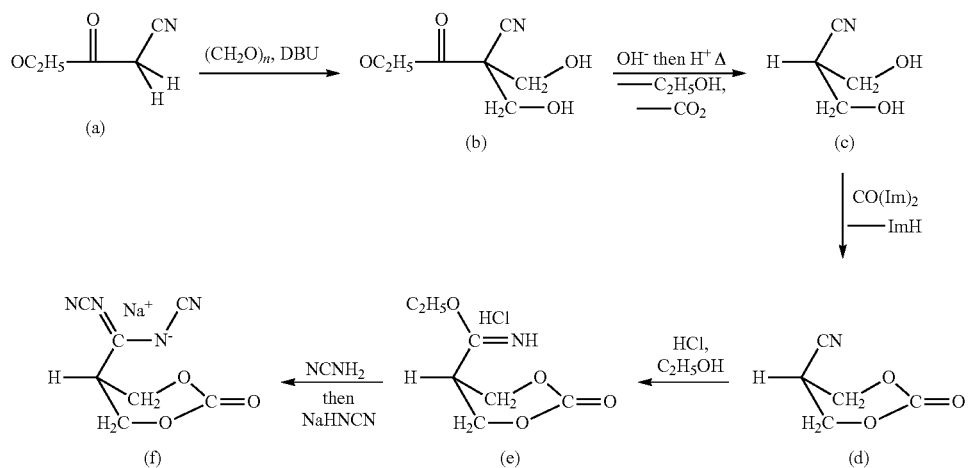

The OH groups are deprotected with Ca(OH)$_2$, and then the compound is treated with HSO$_2$NH$_2$ and B(OH)$_3$ so as to obtain the IB-22 boron complex. The reaction scheme is given below.

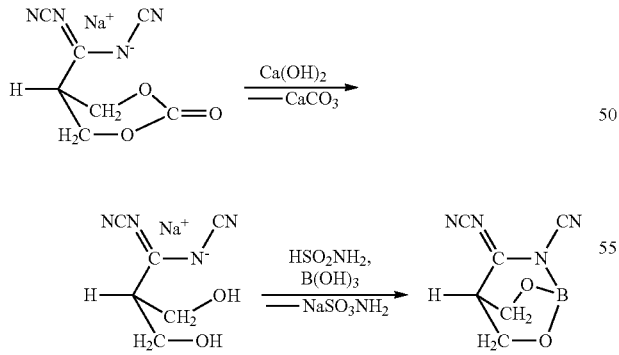

The IB-22 complex is soluble in polar solvents such as acetonitrile, THF, glymes, DMF, DMAc, NMP, DMSO and sulfolane. It forms adducts with NaF, KF, NaCN, KCN, KNCO, NaNCO and NaN$_3$, and with the onium salts of the anions O$^{2-}$, O$_2^{2-}$, O$_2^{\bullet-}$, OH$^-$, RO$^-$, N$_3^-$, CN$^-$, HNCN$^-$ or NCN$^{2-}$.

Example 23

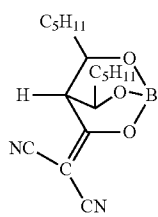

IB-23

A solution of 16 g of monoethyl malonate HO$_2$CCH$_2$CO$_2$C$_2$H$_5$ in 75 ml of pyridine containing 5 drops of diazabicyclo[5.4.0]undec-7-ene was prepared, and was thermostatted at 60° C. with stirring. 20 g of hexanal C$_5$H$_{11}$CHO were added, and the mixture was left to react for 2 hours. The compound HC[CH(C$_5$H$_{11}$)OH]$_2$CO$_2$C$_2$H$_5$ is formed by simultaneous substitution of the acid H and decarboxylation. 7 g of KOCH$_3$ and 6.6 g of malononitrile CH$_2$(CN)$_2$ are added to the solution cooled to 10° C. and under nitrogen bubbling. After 1 hour, the pyridine is evaporated off and a compound K{HC[CH(C$_5$H$_{11}$)OH]$_2$COC(CN)$_2$} is recovered in the form of a solid. This compound is purified by dissolution in acetonitrile and precipitation from toluene.

3.46 g of this salt are added to absolute ethanol, followed by 971 mg of sulfamic acid HSO$_3$NH$_2$ and 970 mg of B(OH)$_3$. The solvent is then eliminated by evaporation and the IB-23 boron complex is recovered.

Example 24

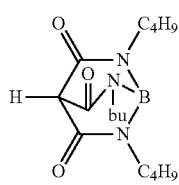

IB-24 tris(N-n-Butylmethanetricarboxamide) HC[CON(C$_4$H$_9$)H]$_3$ was prepared according to the method of D. Prelicz et al., [*Akad. Med. Wroclaw*, Wroclaw, Pol. Roczniki Chemii (1970), 44(1), 49-59] by reacting n-butylamine with commercially available triethyl(methanetricarboxylate). The product is characterized by NMR in DMSO-D$_6$ and its melting point corresponds to that of the literature (182° C.). 3.13 g of the triamide are dissolved in 20 ml of absolute methanol, to which are added 618 mg of boric acid, which go into solution. After the solvent has been evaporated off, the IB-24 complex is obtained.

This complex forms adducts with KF, KOCN, NaCN, KCN, NaOH and KOH, these adducts being soluble in polar solvents such as DMF, DMAc, NMP, sulfolane, acetone, methyl ethyl ketone (MEK), cyclopentanone and acetonitrile. The IB-24 complex forms adducts with onium salts, said adducts being soluble in the abovementioned polar solvents, and also in dichloromethane, chloroform and α,α,α-trifluorotoluene.

The above procedure was reproduced, with the commercially available triethyl(methanetricarboxylate) being replaced with the methylated derivative CH$_3$C(CO$_2$C$_2$H$_5$)$_3$ (prepared by reacting KF and methyl sulfate and treating with 4-cyanoaniline), and the IB-24' complex was obtained.

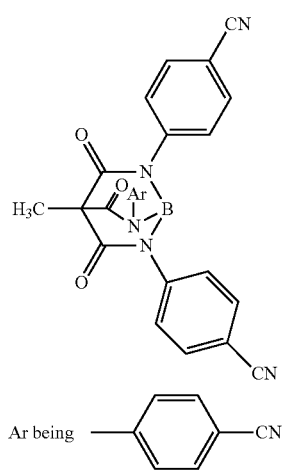

Example 25

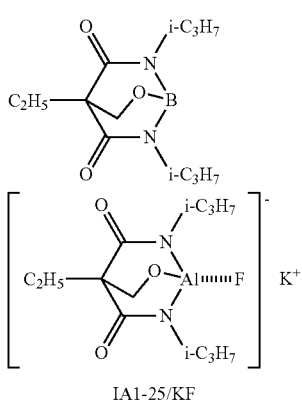

IA1-25/KF 3 g of paraformaldehyde and 15 drops of DBU are added to 18.82 g of commercially available diethyl ethylmalonate CH(C$_2$H$_5$)(CO$_2$C$_2$H$_5$)$_2$. An exothermic reaction takes place, the paraformaldehyde goes into solution, and the compound C$_2$H$_5$C(CH$_2$OH)(CO$_2$C$_2$H$_5$)$_2$ is obtained. 12 g of isopropylamine are then added, and the container is closed and maintained at 40° C. for 72 hours. The excess isopropylamine and the ethanol are evaporated off under vacuum, and the ligand C$_2$H$_5$C(CH$_2$OH)[CON(i-C$_3$H$_7$)H]$_2$ is obtained and is subsequently recrystallized from a toluene-ethanol mixture.

12.2 g of this complex and 7.3 g of triethyl borate B(OC$_2$H$_5$)$_3$ are mixed and the reaction leads to the formation of a liquid, which is a concentrated solution of the IB-25 complex in the ethanol simultaneously formed.

In a glovebox under a neutral atmosphere, 4.18 g of aluminum isopropoxide and 1.18 g of KF are added to 5 g of the ligand C$_2$H$_5$C(CH$_2$OH)[CON(i-C$_3$H$_7$)H]$_2$ in 25 ml of anhydrous DMF, and then the mixture is stirred for 2 hours. A concentrated solution of the complex is obtained, and the result is a solution of the IAl-25-KF adduct.

Example 26

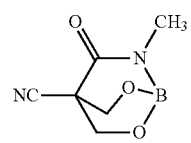

IB-26

11.31 g of commercially available ethyl cyanoacetate are hydroxymethylated with two equivalents (6 g) of paraformaldehyde in the presence of a 1% (molar) catalytic amount of DBU, so as to obtain the diol ester NCC(CH$_2$OH)$_2$CO$_2$C$_2$H$_5$. In the same container, 9 ml of a commercially available aqueous solution containing 40% methylamine are added. Heat is given off over a few minutes and the stirring is maintained for 12 hours. 6.18 g of boric acid are added, and go into solution. The solvent (water of the solution of amine+ethanol formed during the reaction) is evaporated off, and the IB-26 complex is obtained in the form of a colorless solid. This complex forms adducts with KF, KOCN, NaCN, KCN, NaOH, KOH and onium fluorides.

Example 27

10.5 g of commercially available tetrachloroterephthalonitrile are dispersed in 75 ml of DMF with 10 g of potassium fluoride KF. 3.1 g of the IB-4 complex are added to the suspension and the B/F ratio is 1/7. The suspension is stirred at 65° C. for 25 hours. The mixture is filtered, the solid is washed with twice 15 ml of DMF and the filtrate is precipitated from 1 L of water and separated by centrifugation. The product obtained is tetrafluoroterephthalonitrile which is 98% pure as determined by NMR. The filtration residue is constituted of pure KCl, as determined by X-ray spectrometry. Under similar conditions, the tetrachloroterephthalonitrile+KF mixture shows no KCl X-ray line at 65° C. after 25 hours.

Example 28

In a Parr® reactor lined with a polytetrafluoroethylene (PTFE) vessel, flushed by nitrogen sparging and closed, 50 g of pentachloropyridine, 60 g of KF and 7.3 g of the IB-3 complex are introduced into 250 ml of N-methylpyrrolidinone (NMP), the B/F ratio being 1/20. The reactor is brought to 180° C. and maintained at this temperature for three hours, then the heating is stopped, and, after a return to the normal temperature, the reactor is opened. The reaction mixture is filtered and washed with 2×30 ml of NMP. The solid obtained is KCl (74 g, characterized by X-ray analysis). The filtrate is distilled and 28.3 g (84% yield) of pentafluoropyridine ($B_p$=84° C.) are obtained.

Example 29

The present example concerns a Halex reaction on a substrate that is readily activated due to the negative charges borne by the carboxylate groups.

22.9 g of $KHCO_3$ are added to 55 g of commercially available tetrabromoterephthalic acid suspended, with stirring, in 150 ml of water. The clear solution obtained once no more $CO_2$ is being given off is evaporated in an oven at 100° C. The solubility of potassium tetrabromoterephthalate $C_8Br_4O_4K_2$ obtained is 7 g/l in DMF at 25° C.

4.5 g of KF and 0.55 g of the IB-2 complex are added to 10 g of the $C_8Br_4O_4K_2$ salt in 20 ml of DMF, and the mixture is introduced into a Parr® laboratory reactor, of 50 ml, under an $N_2$ pressure, and the reactor is closed. The B/F ratio is 1/20. The reaction is carried out at 200° C. for 5 hours. After cooling, the reactor is open and the suspension is filtered. The filtrate is precipitated from 75 ml of dichloromethane. The potassium tetrafluoroterephthalate $C_8F_4O_4K_2$ yield is 5.2 g (92% of the theoretical yield).

Example 30

11 g of KF and 2.4 g of the IB-4 complex, the B/F ratio being 1/10, are added to 15 g of commercially available tetrachloroterephthalic acid dimethyl ester in 50 ml of DMF. The mixture is stirred at normal temperature for 24 hours. The resulting suspension is run into 200 ml of water and the nonaqueous phase is extracted with 4×30 ml of hexane. The aliquot parts are mixed, the solvent is evaporated off and the residue is distilled at 146° C. under standard pressure. 8.6 g (72% yield) of tetrafluoroterephthalic acid dimethyl ester are obtained.

Example 31

20 g of potassium fluoride and 3.25 g of the IB-2 complex, the B/F ratio being 1/15, are added to 20 g of commercially available 1,2,4-trichlorobenzene in 70 ml of sulfolane (tetramethylene sulfone). The mixture is introduced into a Parr® reactor which is sealed after sparging and flushing with nitrogen, and then brought to 245° C. and maintained at this temperature for 3 hours. The reactor is then cooled to normal temperature and, after opening, the reaction products are filtered. 24.2 g of KCl are obtained. The filtrate is extracted with 5×30 ml of pentane, which is immiscible with sulfolane, the aliquot parts are mixed and the solvent is evaporated off under reduced pressure. 10.5 g (78% yield) of 1,2,4-trifluorobenzene ($B_p$=90° C.) are obtained.

Example 32

2.4 g of KF and 140 mg of the IB-2 complex, corresponding to a B/F ratio of 1/40, were added to 2.65 g of tetrachloroterephthalonitrile in 15 ml of DMF. The suspension was stirred at 30° C. for 24 hours, and then the reaction medium was run into 100 ml of water. The yellow powder formed was recovered by filtration. The tetrafluoro-terephthalonitrile yield is 95%.

By comparison, the process described in WO2002/028822, which is based on a Halex reaction, is carried out on the same substrate, but under much more severe conditions, namely a temperature of 130° C., with a dry DMF having less than 100 ppm of water, and with KF dried by spray drying. These draconian conditions are not necessary when the complexes of the present invention are used.

Example 33

This example and the following two examples illustrate the use of the complexes of the invention for "Halex"-type chlorine→fluorine exchanges in which the complex is used in a stoichiometric amount so as to allow reactions which are impossible with the prior art owing to the sensitivity of the substrates to the elimination reactions.

20 g of epichlorohydrin and 44 g of $K^+[C_2H_5C(CH_2O)_3 BF]^-$, which is the adduct formed by the IB-2 compound with KF, are added to 150 ml of DMF and brought to 85° C. KCl is gradually formed and the reaction mixture is filtered after two hours of stirring. 14 g of epifluorohydrin (88% yield) are obtained by precipitation from 500 ml of water and then filtration.

Example 34

6.9 g of $K^+[C_2H_5C(CH_2O—)_2(CO_2—)BF]^-$, which is the adduct formed between KF and the IB-4 complex, and 2 g of commercially available poly(vinyl chloride) ($M_w$ 45 000) are added to 50 ml of DMF. The suspension is heated with stirring at 75° C. The polymer goes into solution and a white KCl precipitate gradually appears. After reaction for 24 hours, the mixture is filtered and the polymer is precipitated with 200 ml of water. The flocculant powder obtained is filtered off, washed with water and dried. The elemental analysis indicates 96% substitution of the chlorine with fluorine. The absence of coloration of the polymer proves that there is no dehydrochlorination with appearance of a black color, which is the predominant reaction in the presence of KF and DMF in the absence of the complex of the invention.

Example 35

1.7 g of NaF were added to 2.65 g of tetrachloroterephthalonitrile in 15 ml of DMF and the suspension formed was heated in a sealed flask at 65° C. for 48 hours. A small fraction of the reaction medium was collected and the solids were centrifuged and then washed. An X-ray analysis of the powder shows that it is 100% NaF, which signifies that there was no reaction at 65° C.

150 mg of the IB-11 complex was added (so as to obtain a B/F ratio of 1/41.5). The suspension obtained is stirred for a further 24 hours, after which time the analysis of small fractions shows the formation of NaCl. The reaction is continued, and it is observed that, after a further 5 days, there is total conversion of tetrachloroterephthalonitrile to tetrafluoroterephthalonitrile.

NaF is virtually never mentioned in the prior art for Halex reactions owing to the fact that it is completely insoluble in aprotic solvents. However, the use of NaF is advantageous because of its nonhygroscopic nature and its low cost, compared with KF. When NaF is used in place of KF, it is not necessary to take precautions to dry the solvents. The complexation of NaF for a complex of the invention allows its use for Cl—F exchanges.

The activity of the complex of the monoacid $[CH_3C(CH_2O—)_2(CO_2—)]B$ IB-3 was compared with that of the complex of the diacid $[CH_3C(CH_2O—)(CO_2—)_2]B$ IB-11. The two complexes were used to catalyze a Halex reaction carried out with NaF, and a Halex reaction carried out with KF, the reticular energy of which is less than that of NaF. It was apparent that the monoacid is effective when KF is used, but ineffective when NaF is used. The complex of the diacid, including in catalytic amounts, allows the use of NaF, but at relatively low temperatures, owing to its limited thermal stability (100° C.).

Example 36

5 g of the IB-18 complex are dissolved in 40 ml of DMF and 1.70 g of KF are added. The salt rapidly goes into solution in the form of the $K^+\{C_2H_5C(CH_2O—)_2[C(CH_3)_2O—]BF\}^-$ complex. The solution is added to 2.5 g of poly(epichlorohydrin) (commercially available polymer, $M_w \approx 10^6$) in 50 ml of DMF, and the mixture is brought to 85° C. A KCl precipitate is formed after 2 hours and the reaction is continued for 24 hours. The reaction mixture is then run into 100 ml of water and the precipitated polymer is filtered off and washed with water. The elemental analysis shows that 86% of the chlorine atoms of the polymer have been substituted with fluorine atoms without chain degradation. The absence of vinyl ether bonds originating from the elimination of HCl is verified by IR. The same attempt at substitution with KF in DMF at 85° C. gives 100% elimination. This example shows the nucleophilic but nonbasic nature of the adducts of the invention.

Example 37

15.7 g of commercially available ethyl dichloroacetate were dissolved in 100 ml of dimethylacetamide, and 12 g of KF and 3.1 g of IB-4 complex were added, so as to have an F/B ratio=4, i.e. in the catalytic mode. The mixture was introduced into a closed reactor and stirred at 75° C., and then allowed to cool to ambient temperature. The KCl precipitate formed was eliminated by filtration, and the remaining solution was run into 150 ml of water, and then extracted with 3×20 ml of diethyl ether. The ether was then eliminated under vacuum, and the ethyl difluoroacetate was distilled under ambient pressure. The boiling point is 97° C.

Ethyl difluoroacetate is an important starting product for the preparation of pesticides and pharmaceutical products. In addition, it is useful as an additive for reducing impedance and the formation of dendrites during the depositing of lithium metal for lithium batteries.

The process of the invention advantageously replaces the process used in industry, consisting in reacting ethyl chlorodifluoroacetate with zinc in the alcohol.

Example 38

The IB-23 complex is used for phase-transfer catalysis in a Halex reaction.

20 g of 4-chloro-meta-dinitrobenzene $(NO_2)_2C_6H_3Cl$ were dissolved in 100 ml of α,α,α-trifluorotoluene, and an aqueous solution containing 500 mg of the IB-23 complex, 500 mg of tetrapropylammonium bromide and 7 g of KF were added with stirring at 80° C. The two-phase system was left to react for 12 hours, and then the trifluorotoluene was eliminated by evaporation under reduced pressure.

15.6 g (yield of 84%) of 4-fluoro-1,3-dinitrobenzene $(NO_2)_2C_6H_3F$ were obtained.

The procedure was reproduced, with the boron complex being omitted. No reaction was observed.

Example 39

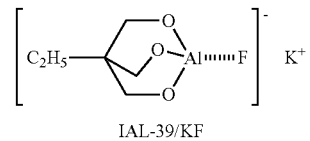

IAl-39/KF

A catalytic Halex reaction was carried out with a IA1-39/KF adduct prepared in situ.

Carrying out the procedure in a glove box under an inert atmosphere, 2.03 g of aluminum isopropoxide, 2.34 g of potassium fluoride and 2.65 g of tetrachloro-terephthalonitrile were added to 1.34 g of 2-ethyl-2-hydroxymethyl-1,3-propanediol $C_2H_5C(CH_2OH)_3$ in 15 ml of anhydrous DMF. The F/Al ratio is 4/1. The suspension is stirred at 75° C. for 24 hours. An X-ray spectrum shows the absence of KF and the presence of KCl originating from the Halex exchange, and which shows that tetrafluoroterephthalonitrile was obtained.

Under the same conditions, the complex of aluminum and bis(hydroxymethyl)butyric acid gives 100% exchange after 48 hours at 75° C. The adduct of this complex is obtained under the same conditions as the IAl-39/KF adduct, with $C_2H_5C(CH_2OH)_3$ being replaced with $C_2H_5C(CH_2OH)_2COOH$.

Example 40

Tetrachloro-N-methylpyrrole is prepared by chlorination of commercially available N-methylpyrrole with sulfuryl chloride $SOCl_2$ in acetonitrile.

1.4 g of the IB-2 complex and 2.7 g of dry KCN are added to a solution of 2.19 g of N-methylpyrrole in DMF, such that the CN/B ratio is 4/1. The mixture is left to react at 65° C. for 8 hours with magnetic stirring. 820 g of NaSCN are then added and stirring of the reaction medium is continued for 24 hours at 65° C.

After cooling, the reaction mixture is run into 100 ml of water and the pH is adjusted to 0 by adding sulfuric acid in a well-ventilated hood. The solution is extracted with 4×20 ml of diethyl ether. The fractions are combined and the solvent is eliminated by evaporation. 1.23 g (73% yield) of tetracyanopyrrole are obtained. The reaction scheme is as follows:

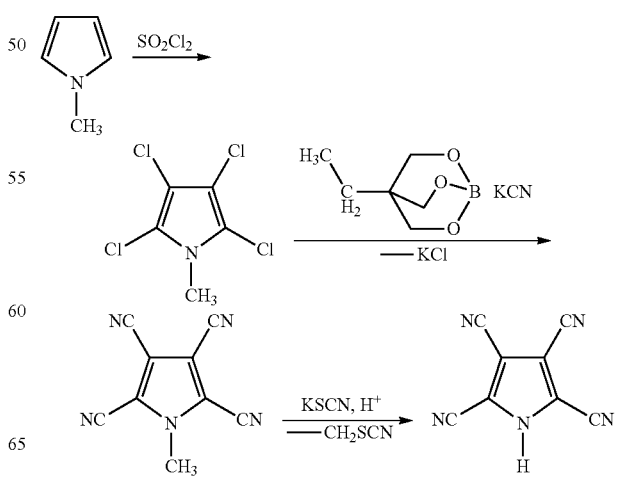

Tetracyanopyrrole is a strong Brønsted acid, the lithium salt of which is strongly dissociated in organic aprotic solvents and in solvating polymers such as polyethers of which the majority of the recurring units are ethylene oxide units. The lithium salt of tetracyanopyrrole is particularly useful as salt of the electrolyte of a lithium battery, alone or as a mixture with other salts.

Example 41

Propylmethylpyrrolidinium bromide was prepared by Menshutkin reaction of N-methylpyrrolidine with 1-bromobutane. 21.5 g of the adduct formed by the IB-4 complex with KF were added to 20.8 g of $[C_4H_8N(CH_3)C_3H_7]Br$ in 100 ml of acetone. The suspension was stirred by means of a magnetic stirrer for 48 hours. The KBr formed during the reaction was eliminated by filtration and the precipitate was washed with two portions of 20 ml of acetone. The solvent was eliminated and a viscous liquid was recovered, corresponding to the formula:

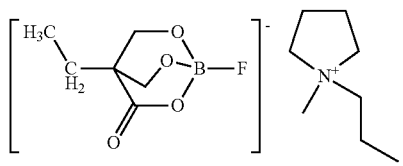

This salt can be used as a reactive medium for a fluorination according to the Halex reaction, owing to its high thermal stability and its low vapor pressure. It can also, in the presence of an alkaline metal fluoride, in particular of KF, bring about the dehaloflourination of various substrates.

Example 42

24.6 g of the sodium fluoride adduct of example 17, $Na^+\{[C_2H_5C(CH_2O—)_2C[C(CN)_2]O—]BF\}^-$, are added to 14.7 g of ethylmethylimidazolium chloride in 120 ml of acetonitrile. The mixture is stirred at ambient temperature for 4 hours and then the suspension obtained is filtered. The solvent is eliminated and a colorless viscous liquid is obtained, corresponding to the compound:

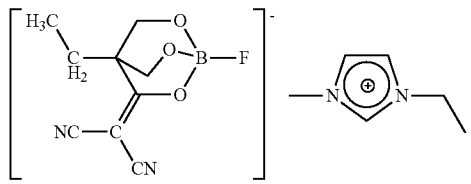

This ionic liquid is stable at 285° C. with less than 5% loss of weight. It can be used as a solvent for a Halex reaction as in example 36.

Example 43

Preparation of FeOCl

In a glass vial and carrying out the procedure in a glove box, 10 g of nanometric $Fe_2O_3$ [obtained by pyrolysis at 400° C., under air, of ferrous oxalate $Fe(C_2O_4)_2.2H_2O$] and 11.2 g of anhydrous $FeCl_3$ (10% excess) are mixed and the vial is stoppered, taken out of the glove box and sealed under vacuum using a blowtorch. The vial is maintained at 300° C. in an oven for 24 hours, and then cooled and opened. The FeOCl obtained is washed on a filter with methyl formate and a reddish-violet powder is obtained. The X-ray characterization of the powder shows that it is FeOCl with an orthorhombic structure, for which a=3.75 Å, b=3.3 Å, c=7.95 Å; SG: Pmmn (59).

Fluorination of FeOCl with IB-11/LiF 214 mg of FeOCl, 52 mg of lithium fluoride LiF and 22 g of the boron complex $[CH_3C(CF_{12}O—)(CO_2—)_2]B$ (IB-11) are mixed in 13 ml of DMF in a glove box under a neutral atmosphere. The mixture is stirred for 23 hours at 75° C. The X-ray analysis of the product obtained shows the disappearance of FeOCl and the appearance of an orthorhombic FeOF phase, a=6.6039 (0) Å, b=12.8946 (0) Å, c=4.67223 (0), never described.

Fluorination of FeOCl with IB-3/Et$_4$NF

The IB-3/Et$_4$NF adduct was prepared by adding 1.85 g (1 mmol) of commercially available tetraethylammonium fluoride in dihydrate form and 1.42 g of the IB-3 complex to 25 ml of ethanol. Next, the solvent is evaporated off in a rotary evaporator, and the product obtained is dried under vacuum at 60° C. for 25 hours.

0.54 g of FeOCl (5 mmol) is mixed with 1.635 mg (5 mmol) of the IB-3/Et$_4$NF adduct in 60 ml of DMF in a Parr® bomb, the procedure being carried out in a glove box under argon. The reaction mixture is stirred at 150° C. for 48 hours, and then filtered and washed with 20 ml of methyl formate. The compound obtained has the same structural characteristics as that obtained with the IB-11/LiF adduct.

Example 44

A liquid electrolyte was prepared by dissolving 2.3 g of the adduct formed by the IB-14 boron complex with LiF in 10 ml of a 50/50 by volume mixture of methyl carbonate and ethylene carbonate. The conductivity of the electrolyte is 3 mScm$^{-1}$.

A battery is produced using a lithium metal foil (having a thickness of 200 μm and a diameter of 1.8 cm), a glass-fiber separator having the same diameter and a composite positive electrode comprising 75% by weight of CuF$_2$, 15% by weight of acetylene black and 10% by weight of poly(vinylidene fluoride) PVF$_2$. The suspension with this composition is spread, using a solution of PVDF in NMP, on an aluminum collector and to evaporated. The active mass of CuF$_2$ is 18 mg. The battery is assembled in the form of a button cell. The separator is impregnated with 10 drops of electrolyte and then sealed by stamping, in a glove box.

The battery is discharged under a direct current of 10 μA at 25° C. and shows a capacity of 8.46 mAh (86% of the theoretical capacity) at a low cutoff potential of 2.5 V. The battery can be cycled between 2.5 and 3.8 V vs Li$^+$:Li°, conserving 65% of the capacity at the 1st charge after 50 cycles.

Example 45

A lithium-air battery was produced using:
- an anode constituted of a lithium metal foil (having a thickness of 200 μm and a diameter of 1.8 cm);
- a cathode constituted of a porous composite material containing 48% by weight of carbon black, 2% by weight of dilithium phthalocyanin, 10% by weight of carbon nanotubes, and 30% by weight of polytetrafluoroethylene (PTFE) latex bound by an ethylene/propylene random polymer (10%), said composite material being deposited on a collector made of Exmet® expanded aluminum using a solution in cyclohexane;

a separator impregnated with 0.8 M solution of Li[(CF$_3$SO$_2$)$_2$N] in an ionic liquid constituted of the bis(fluorosulfonimide) salt [(FSO$_2$)$_2$N]$^-$ of N-methyl-N-propyl-pyrrolidinium (MePrPy)$^+$ to which 0.3 M of the IB-19 boron complex has been added. The boron complex is intended for forming complexes with the products of oxygen reduction at the air electrode.

The battery operates at a discharge potential of 2.8 V and is recharged at a potential of 3.5 V with a current density of 100 μm A.cm$^{-2}$. The recharge potential in a similar battery, but containing no complex, is 4.5 V.

The soluble species present in the electrolyte of the battery containing the boron complex are indicated hereinafter.

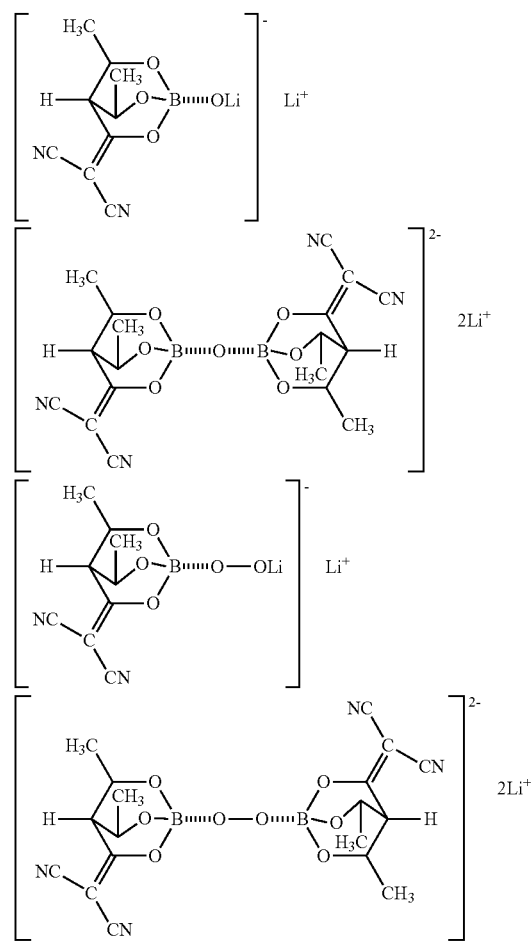

Example 46

A battery was produced using a lithium anode, a separator and a composite cathode.

The anode is obtained using a lithium metal foil having a thickness of 60 μm rolled on a copper foil of 25 μm and cut to a diameter of 1.8 cm. The separator is constituted of a microporous polyolefin (Celgard®) having the same diameter. The composite positive electrode is obtained by spreading, on a 25 μm aluminum current collector, a composition containing 75% by weight of graphite fluoride CF$_y$ (y≈0.25), 15% by weight of acetylene black and 10% by weight of carboxymethylcellulose (CMC) in suspension in water, and then evaporating off the water. The active mass of CF$_x$ in the cathode is 7.5 mg.

The electrolyte is constituted of a solution of the IB-14"/LiF adduct formed by the IB-14" complex with LiF.

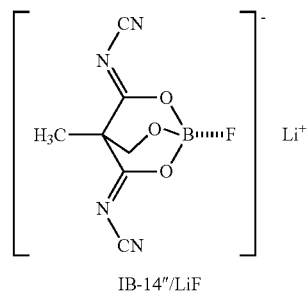

IB-14"/LiF

The concentration of adduct is 1 mol/l in a 50/50 by volume mixture of ethylene carbonate/dimethyl carbonate.

The battery is assembled in the form of a button cell. The separator is impregnated with 8 drops of electrolyte, and then sealed by stamping, in a glove box. It is cycled between 2.5 and 4.2 V according to the reaction:

$$CF_y + yLi^+ + ye^- \Leftrightarrow yLiF + C$$

and it is noted that the cycling is carried out with a capacity of 330 mAh/g of CF$_y$.

A battery was assembled in the same way, but omitting the adduct. It was noted that the above reaction is irreversible, which is the result of the insolubility of LiF in the absence of boron complex.

Example 47

5.4 g of sodium methoxide are added, in small portions, with stirring, to 17.4 g of commercially available diethyl (methyl) malonate CH(CH$_3$)(CO$_2$C$_2$H$_5$)$_2$ in 75 ml of anhydrous THF cooled to 0° C. 12.2 g of ethyl chloroacetate ClCH$_2$CO$_2$C$_2$H$_5$ are added, dropwise, over a period of one hour, to the light solution obtained. The reaction mixture is left to stir at normal temperature for 24 hours. The sodium chloride precipitate formed is filtered off and the THF is eliminated on a rotary evaporator. The yield of 1,2,2-tri (ethoxy-carbonyl)propane (CH$_3$)C(CH$_2$CO$_2$C$_2$H$_5$)(CO$_2$C$_2$H$_5$)$_2$ is 96%.

13 g of this triester in 40 ml of anhydrous ethanol are treated with 6.4 g of sodium hydroxide with stirring. After 24 hours, the white precipitate of (CH$_3$)C(CH$_2$CO$_2$Na)(CO$_2$Na)$_2$ is filtered off and washed with three portions of 20 ml of ethanol and dried under vacuum. 8.07 g of this salt are dissolved in 20 ml of water, and 4.9 of sulfuric acid and 2.06 g of boric acid are added. The solution is evaporated to dryness and the residue is taken up with 15 ml of anhydrous ethanol and filtered. After drying, 4.4 g of the CH$_3$C(CH$_2$CO$_2$—)(CO$_2$—)$_2$B complex of IIB type are obtained.

Example 48

13 g of 1,2,2-tri(ethoxycarbonyl)propane (CH$_3$)C(CH$_2$CO$_2$C$_2$H$_5$)(CO$_2$C$_2$H$_5$)$_2$ of the triester of example 1 are hydrolyzed with 9 g of potassium hydroxide in 50 ml of methanol, with the temperature being maintained at 10° C. The precipitate of the potassium salt (CH$_3$)C(CH$_2$CO$_2$K)(CO$_2$K)$_2$ is filtered off and washed with three portions of 20 ml of isopropanol and dried under vacuum.

2.90 g of said salt, 2.41 of aluminum chloride hexahydrate $AlCl_3.6H_2O$ and 600 mg of potassium fluoride are reacted in 20 ml of a 50/50 mixture of isopropanol and acetonitrile. The KCl precipitate and the excess KF are eliminated by filtration and the solvent is evaporated off so as to give the adduct $\{CH_3C(CH_2CO_2—)(CO_2—)_2AlF\}^-K^+$ of the IIA1/KF type. This salt is very soluble in DMF and partially soluble in the 50/50 EC-DMC mixture of carbonates.

Example 49

Figure 2:
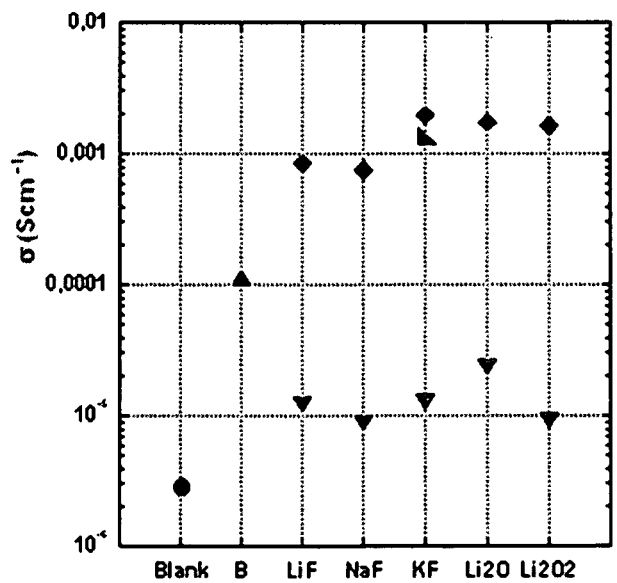

Measurements of conductivity at 25° C. were carried out on the boron complex of example 1 and the adduct with KF of the aluminum complex of example 2, in, firstly, an ethyl carbonate/dimethyl carbonate (EC/DMC) mixture and, secondly, in dimethylformamide (DMF). The results are represented in FIGS. 1 and 2. FIG. 1 corresponds to the results obtained from solutions in the EC/DMC mixture and FIG. 2 to those obtained from solutions in DMF. In each of the figures, the conductivity a, expressed in $Scm^{-1}$, is given along the y-axis and:
- the "Blank" column gives the conductivity of the solvent, at the point marked ●.
- The "B" column gives the conductivity of a 1M solution of the boron complex, at the point marked ▲.
- The LiF column gives the conductivity of a solution saturated with LiF at the point marked ▼, and the conductivity of a 1M solution of complex, saturated with LiF, at the point marked ♦.
- The NaF column gives the conductivity of a solution saturated with NaF at the point marked ▼, and the conductivity of a 1M solution of complex, saturated with NaF, at the point marked ♦.
- The KF column gives the conductivity of a solution saturated with KF at the point marked ▼, the conductivity of a 1M solution of complex, saturated with KF, at the point marked ♦, and the conductivity of a 1M solution of adduct of KF with the aluminum complex at the point marked ▲.
- The $Li_2O$ column gives the conductivity of a solution saturated with $Li_2O$ at the point marked ▼, and the conductivity of a 1M solution of complex, saturated with $Li_2O$, at the point marked ♦.
- The $Li_2O_2$ column gives the conductivity of a solution saturated with $Li_2O_2$ at the point marked ▼, and the conductivity of a 1M solution of complex, saturated with $Li_2O_2$, at the point marked ♦.

These results show the substantial improvement in the conductivity of various salts provided by the presence of a complex according to the invention, this increase in conductivity resulting from an increase in the solubility. This characteristic is important when the compounds are used in the electrolyte of an electrochemical generator, such as a battery or a fuel cell.

Example 50

10 g of commercially available sodium monocyanamide NaHNCN are added to 13 g of 1,2,2-tri(ethoxycarbonyl)propane $(CH_3)C(CH_2CO_2C_2H_5)(CO_2C_2H_5)_2$ in 75 ml of anhydrous ethanol. The reaction mixture is maintained at 40° C. with stirring for 48 hours and the white precipitate which forms is centrifuged, washed with three portions of 25 ml of isopropanol, and then dried under vacuum at 60° C. 3.14 g of the $(CH_3)C[CH_2C(NCN)ONa][C(NCN)ONa]_2$ salt obtained, 2.92 g of sulfamic acid $NH_2SO_3H$ and 1.46 g of triethyl borate $B(OC_2H_5)_3$ are dispersed in 15 ml of ethanol. The reaction mixture is stirred at normal temperature for 24 hours, filtered, evaporated, and then dried under a primary vacuum at 75° C.

The complex $\{(CH_3)C[CH_2C(NCN)O—][C(NCN)O—]_2\}B$ of IIB type is obtained with a yield of 88%. This complex forms adducts with LiF, NaF, KF, LiCl, NaCl, KCl, $Li_2O$, $Li_2O_2$, $Na_2O_2$, NaOCN, KOCN, $NaN_3$, $KN_3$, NaCN and KCN, which are soluble in polar aprotic solvents.

Example 51

10.5 g of malononitrile, $CH_2(CN)_2$, 16 g of triethylamine and 20 g of anhydrous calcium trifluoroacetate $Ca(CF_3CO_2)_2$ are added to 13 g of 1,2,2-tri(ethoxycarbonyl)-propane $(CH_3)C(CH_2CO_2C_2H_5)(CO_2C_2H_5)_2$ in 75 ml of anhydrous ethanol and under a nitrogen atmosphere. The mixture is stirred at normal temperature and a white precipitate forms in 24 hours. The precipitate is centrifuged, washed with three portions of 25 ml of isopropanol and then dried under vacuum at 60° C.

7.3 g of the $\{(CH_3)C[CH_2C(C(CN)_2)O][C(C(CN)_2)O]_2\}_2Ca_3$ salt obtained are dispersed in 25 ml of ethanol, and 4.62 of aluminum sulfate hydrate $Al_2(SO_4)_2.12\ H_2O$ are added to the reaction medium, which is then stirred at normal temperature for 12 hours, filtered to eliminate the calcium sulfate, evaporated, and then dried under a primary vacuum at 60° C. The complex $\{(CH_3)C[CH_2C(C(CN)_2)O—][C(C(CN)_2)O—]_2\}Al$ of IIA1 type) is obtained with a yield of 82%.

This complex forms adducts with LiF, NaF, KF, LiCl, NaCl, KCl, $Li_2O$, $Li_2O_2$, $Na_2O_2$, NaOCN, KOCN, $NaN_3$, $KN_3$, NaCN, KCN, LiCl, NaCl and KCl, which are soluble in polar aprotic solvents.

Example 52

3.96 g of commercially available diethyl malonate $CH_2(CO_2CH_3)_2$ and 6.5 g of sodium methoxide are added in small portions to 30 ml of anhydrous methanol cooled to 0° C. A solution of 3.67 g of chloroisobutyric acid $Cl(CH_3)_2CCO_2H$ in 10 ml of methanol is added dropwise, over a period of one hour, to the light solution obtained. The reaction mixture is left at normal temperature with stirring for 24 hours. The sodium chloride precipitate formed is filtered off and 3 ml of water are added. After one hour, an $HC[C(CH_3)_2CO_2Na][CO_2Na]_2$ precipitate forms and is extracted after washing in ethanol. 2.56 g of this salt are suspended in 15 ml of isopropanol and 10 ml of a 1M commercially available solution of boron trichloride in dichloromethane are added. The NaCl precipitate is filtered off and a solution of the complex $HC[C(CH_3)_2CO_2—][CO_2—]_2B^-$ (of IIB type) is obtained. This solution is evaporated so as to give a crystalline solid which forms adducts, which are soluble in DMF, with KF, NaF, NaOCN, NaCN, KCN and $NaN_3$.

Example 53

5.22 g of commercially available diethyl(methyl) malonate $CH_3CH(CO_2C_2H_5)_2$ and 5 g of sodium ethoxide are added in small portions to 30 ml of anhydrous ethanol cooled to 0° C. A solution of 3.67 g of bromodifluoroacetic acid $BrF_2CCO_2H$ in 10 ml of ethanol is then added dropwise over a period of one hour. The reaction mixture is left at normal temperature with stirring for 24 hours, and then 3 ml of water are added. After one hour, a $CH_3C[CF_2CO_2Na][CO_2Na]_2$ precipitate forms and is extracted after washing in ethanol so as to eliminate the NaBr formed. 2.78 g of this salt are suspended in 15 ml of isopropanol and 2.41 g of aluminum chloride hydrate are added. The NaCl precipitate is filtered off and a solution of the adduct {Hc[CF$_2$CO$_2$—][CO$_2$—]$_2$AlCl}$^-$Na$^+$ of the aluminum complex (IIA1 type) and of sodium chloride is obtained. When treated with NaF in acetonitrile, this adduct gives {HC[C(CH$_3$)$_2$CO$_2$—][CO$_2$—]$_2$AlF}$^-$Na and an NaCl precipitate.

Example 54

20 drops of 1,8-diazabicyclo[5.4.0]undec-7-ene (DBU) and 6 g of propylene oxide in 25 ml of acetonitrile are added dropwise, by means of a dropping funnel, to 17.42 g of commercially available diethyl(methyl) malonate CH(CH$_3$)(CO$_2$C$_2$H$_5$)$_2$ in 80 ml of acetonitrile, cooled with stirring to 0° C. The reaction product is treated with a rotary evaporator and taken up with 100 ml of water acidulated with 5 ml of commercially available hydrochloric acid, and then extracted with dichloromethane, which is subsequently evaporated off. 1-hydroxy-2-methyl-3,3-di(ethoxycarbonyl)butane (CH$_3$)C[CH(CH$_3$)CH$_2$OH](CO$_2$C$_2$H$_5$)$_2$ is obtained with a yield of 88%.

10 g of the alcohol diester are hydrolyzed in 40 ml of isopropanol with 4 g of LiOH.H$_2$O (proportion 1:2.2) at normal temperature for 12 hours. The white precipitate obtained is centrifuged and washed with three times 20 ml of isopropanol, then dried under a primary vacuum at 60° C. 3.76 g of the resulting salt (CH$_3$)C[CH(CH$_3$)CH$_2$OH](CO$_2$Li)$_2$ are suspended in THF and then treated with 1.96 g of sulfuric acid and 2.91 g of triethyl borate. The Li$_2$SO$_4$ precipitate which forms is eliminated by centrifugation and the complex (CH$_3$)C[CH(CH$_3$)CH$_2$O—](CO$_2$—)$_2$B (IIB type) is obtained in the form of a colorless solid.

Example 55

20 drops of 1,8-diazabicyclo[5.4.0]undec-7-ene and 9 g of ethylene carbonate are added to 18.8 g of commercially available diethyl(ethyl) malonate CH(C$_2$H$_5$)(CO$_2$C$_2$H$_5$)$_2$. The mixture is heated to 165° C. under a nitrogen atmosphere with stirring, and CO$_2$ is given off Once no more gas is being given off (approximately 2 hours), the mixture is cooled and run into 150 ml of water, and the 1-hydroxy-3,3-di(ethoxycarbonyl)pentane alcohol diester of formula C$_2$H$_5$C[C$_2$H$_4$OH](CO$_2$C$_2$H$_5$)$_2$ is extracted with hexane. The yield is 75%.

11.6 g of the alcohol diester are treated in 50 ml of methanol with 6 g of calcium chloride, 4.4 of cyanamide and 12.5 g of tetramethylguanidine at 60° C. for 48 hours. The white precipitate which forms is centrifuged and washed with three times 20 ml of methanol and dried under a primary vacuum at 60° C., so as to give the calcium salt [(C$_2$H$_5$)C[C$_2$H$_4$OH](CONCN)$_2$]Ca.

2.48 g of this salt in suspension in ethanol are treated with 900 mg of anhydrous oxalic acid and 1.04 g of trimethyl borate. The CaC$_2$O$_4$ precipitate is eliminated by centrifugation and the complex C$_2$H$_5$C(C$_2$H$_4$O—)[C(NCN)O—]$_2$B (IIB type) is obtained in the form of a colorless solid after evaporation. After addition of KF, KOCN, NaOCN or NaCN, an adduct is obtained which is very soluble in DMF and in acetonitrile (>10 g/l).

Example 56

17.4 g of diethyl(methyl) malonate diluted in 50 ml of THF are added dropwise to a suspension of 4.8 g of sodium hydride in 50 ml of anhydrous THF cooled to 0° C., followed by 11.6 g of 2-chloroethylamine hydrochloride in small portions, with stirring. After reaction for 24 hours and once hydrogen is no longer being given off, the suspension is filtered so as to eliminate the NaCl formed, and the product is purified by dissolution in 120 ml of 1M HCl, extraction with ether, addition of 15 g of sodium hydrogen carbonate and extraction with dichloromethane, which is subsequently evaporated off.

4.34 g of the resulting amino diester CH$_3$C[C$_2$H$_4$NH$_2$](CO$_2$C$_2$H$_5$)$_2$ are treated in 25 ml of THF with 4 g of trifluoromethanesulfonyl imidazole CF$_3$SO$_2$(C$_3$N$_2$H$_3$), and then 2.0 g of sodium hydroxide and 15 cc of ethanol are added. After 24 hours, the precipitate is centrifuged and washed with three times 15 ml of anhydrous ethanol. Added to 3.6 g of the CH$_3$C[C$_2$H$_4$N(Na)CF$_3$SO$_2$](CO$_2$Na)$_2$ salt in 20 ml of dimethylformamide are 1.42 g of boron trifluoride etherate BF$_3$O(C$_2$H$_5$)$_2$ which reacts according to the following reaction scheme:

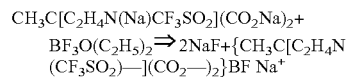

The sodium fluoride is then eliminated by filtration.

Example 57

1,2,2-tri(ethoxycarbonyl)hexane, (C$_4$H$_9$)C(CH$_2$CO$_2$C$_2$H$_5$)(CO$_2$C$_2$H$_5$)$_2$ is prepared from commercially available diethyl (butyl) malonate C$_4$H$_9$CH(CO$_2$C$_2$H$_5$)$_2$ by means of the process of example 1. 30.2 g of this compound in 100 ml of isopropanol are treated with 19.5 g of sodium monocyanamide at 40° C. for 24 hours. The sodium salt (C$_4$H$_9$)C[CH$_2$C(NCN)ONa][C(NCN)ONa]$_2$ which precipitates is centrifuged, washed with three portions of 30 ml of isopropanol, and then dried under vacuum at 50° C.

The aluminum complex {(C$_4$H$_9$)C[CH$_2$C(NCN)O—][C(NCN)O—]$_2$}Al (11A1 type) is prepared in ethanol by reacting 6 g of aluminum sulfate hydrate Al$_2$(SO$_4$)$_2$.12 H$_2$O with 9.24 g of said sodium salt. The sodium sulfate precipitate is eliminated by centrifugation and the solution is evaporated so as to give the aluminum complex, which is dried under a primary vacuum at 75° C.

This complex is soluble in most polar aprotic solvents, such as, for example, acetone, methyl ethyl ketone, acetonitrile, dimethylformamide (DMF), dimethyl sulfoxide (DMSO), cyclic alkyl or fluoroalkyl carbonates (such as dimethyl carbonate, diethyl carbonate, ethylmethyl carbonate, ethylene carbonate, propylene carbonate, fluoroethylene carbonate or fluoromethylethylene carbonate), esters (such as methyl formate and γ-butyrolactone), ethers [such as THF, glycol oligoethers and poly(ethylene oxide)], ionic liquids (such as ethylmethylimidazolium bis(trifluoromethanesulfonyl)imide) and mixtures thereof. The Lewis acid thus prepared forms complexes, which are themselves also soluble in similar solvents, with LiF, NaF, KF, LiCl, NaCl, KCl, Li$_2$O, Li$_2$O$_2$, Na$_2$O$_2$, NaOCN, KOCN, NaN$_3$, KN$_3$, NaCN and KCN, cited in a nonlimiting manner, in the same solvents.

Example 58

2-methylamino-1,3-propanediol is prepared according to the following reaction sequence:
treatment of commercially available ethyl cyanoacetate with two equivalents of paraformaldehyde in the presence of a catalytic base (tetramethylguanidine) according to the reaction:

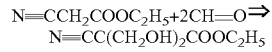

decarboxylation according to the reaction:

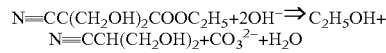

catalytic dehydrogenation according to the reaction:

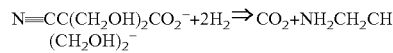

10.5 g of the aminoglycol NH$_2$CH$_2$CH(CH$_2$OH)$_2$ obtained and dissolved in 30 ml of acetonitrile are treated, at 0° C., with 9.9 g of commercially available sulfonyldiimidazole SO$_2$(C$_3$N$_2$H$_3$)$_2$ in 30 ml of ACN, added dropwise, followed by 9.7 g of sulfamic acid. The imidazolium sulfamate precipitate is filtered off and the solution is evaporated. The sulfamide (HOCH$_2$)$_2$C(H)CH$_2$N(H)SO$_2$N(H)CH$_2$C(H)(CH$_2$OH)$_2$ is recrystallized from an isopropanol/toluene mixture, so as to obtain an analytically pure product.

5 g of the sulfamide and 5.36 g of triethyl borate B(OC$_2$H$_5$)$_3$ are mixed in 10 ml of acetonitrile and a clear solution is obtained, which is evaporated.

The dinuclear complex thus formed:

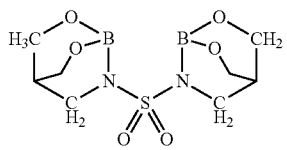

forms adducts with the salts LiF, NaF, KF, NH$_4$F, BaF$_2$, Li$_2$O, Li$_2$O$_2$, Na$_2$O$_2$, NaOCN, KOCN and NaN$_3$ which are soluble in polar aprotic solvents.

Example 59

18 g of itaconic acid dilithium salt H$_2$C=C(CO$_2$Li)(CH$_2$CO$_2$Li) prepared from the commercially available acid and from lithium carbonate are refluxed for two hours in 60 ml of commercially available ammonia solution. The excess ammonia is evaporated off, the solid residue is the salt NH$_2$CH$_2$CH(CO$_2$Li)(CH$_2$CO$_2$Li), 7.94 g of which are suspended in 30 ml of trifluoroethanol, and 4 g of carbonyldiimidazole CO(C$_3$N$_2$H$_3$)$_2$ are added, with stirring. After one hour, 30 mol of dioxane are added and the precipitate is centrifuged and washed with three portions of 20 ml of isopropanol and then dried. After the resulting product has been passed through a Dowex® macroreticular ion exchange resin with SO$_3$H functional groups, the acid (HO$_2$C)$_2$(HO$_2$CCH$_2$)C(H)CH$_2$N(H)—CON(H)CH$_2$C(H)(CO$_2$H)(CH$_2$CO$_2$H) is obtained. After evaporation of the solution having been used for the exchange, the acid is obtained in the form of a white crystalline solid.

3.65 g of this solid and 2.08 g of trimethyl borate are added to 10 ml of methanol. The light solution obtained is evaporated and dried at 80° C. under vacuum, so as to give the complex:

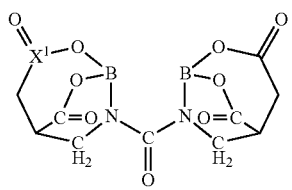

This complex forms adducts with the anions of the salts LiF, NaF, KF, LiCl, NaCl, KCl, LiOH, Li$_2$O, Li$_2$O$_2$, Na$_2$O$_2$ and KO$_2$.

The above procedure was reproduced, with the carbonyldiimidazole being replaced with thiocarbonyldiimidazole, and the corresponding thiourea was obtained:

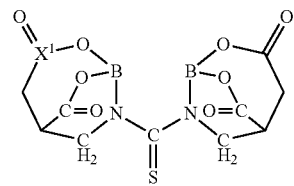

After oxidation and dimerization, this complex gives a dicationic compound which has a very high complexation constant for the Z and Z" anions.

Example 60

0.7 ml of tetramethylguanidine, 4.8 g of sulfamide SO$_2$(NH$_2$)$_2$ and 6 g of paraformaldehyde (CH$_2$=O)$_n$ are added to 17.4 g of commercially available diethyl (methyl) malonate CH(CH$_3$)(CO$_2$C$_2$H$_5$)$_2$ in 40 ml of dimethylformamide. The mixture is stirred at 50° C. for 24 hours, and then run into 150 ml of water. The tetraester is extracted with ether in 3 portions of 40 ml and the extracts are mixed and evaporated so as to give the compound (C$_2$H$_5$O$_2$C)$_2$(CH$_3$)CCH$_2$NHSO$_2$NHCH$_2$C(CH$_3$)(CO$_2$C$_2$H$_5$)$_2$.

The treatment of 4.68 g of tetraester with 6 g of Ca(OH)$_2$ in 20 ml of a 50/50 mixture of ethanol/water gives [(O$_2$C)$_2$(CH$_3$)CCH$_2$NHSO$_2$NHCH$_2$C(CH$_3$)—(CO$_2$C$_2$H$_5$)$_2$]Ca$_2$.

By reacting 910 mg of anhydrous oxalic acid with 2.45 g of the calcium salt and 1.23 g of boric acid, in methanol, the binuclear complex:

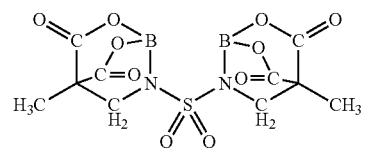 [SMILES: CC12CN(S(=O)(=O)N3CC4(C)C(=O)OB3OC4=O)B(OC1=O)OC2=O]

is obtained in crystalline form after separation of CaC$_2$O$_4$ and evaporation. This complex forms adducts with LiF, NaF, KF, LiOH, Li$_2$O, Li$_2$O$_2$, Na$_2$O$_2$, KO$_2$˙, NaN$_3$, NaCN and KCN.

If Ca(OH)$_2$ is replaced, as hydrolyzing agent, with NaHNCN or LiCH(CN)$_2$, the substitution of C=O with C=NCN or C=C(CN)$_2$ is obtained, thereby increasing the solubility of the corresponding adducts in polar aprotic solvents.

The invention claimed is:

1. A polycyclic complex corresponding to one of the general formulae:

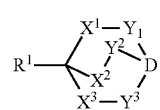 (ID)

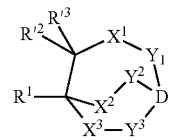 (IID)

-continued

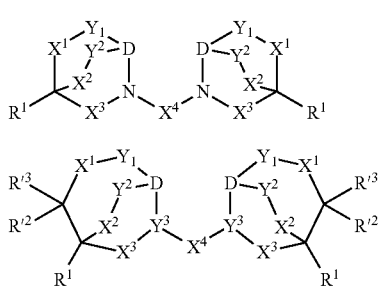

(IIID)

(IVD)

in which:
D represents boron B or aluminum Al;
$R^1$ represents R, $R_F$, $NO_2$, CN, C(=O)OR, $RSO_2$ or $R_FSO_2$;
each of the —$X^1$—, —$X^2$—, —$X^3$— and $X^4$ groups represents, independently of the others, a >C=O, >C=NC=N, >C=C(C=N)$_2$, >$CR^2R^3$ or >$SO_2$ divalent group;
each of the —$Y^1$—, —$Y^2$— and —$Y^3$— groups represents, independently of the others, an —O—, >N(C=N), >N(COR$_F$), >N(SO$_2$R$^4$), >NR$^4$, >N(COR$^4$) or >N(SO$_2$R$_F$)divalent group;
R, $R^2$ and $R^3$ each represent, independently of the others, H, an alkyl group, an aryl group, an alkylaryl group, an arylalkyl group, an oxaalkyl group or an alkenyl group;
$R^4$ represents an alkyl group, an aryl group, an alkylaryl group, a heteroaryl group, an arylalkyl group, an oxaalkyl group, an alkenyl group or an $R_FCH_2$ group;
$R_F$ is a perfluoroalkyl group or a partially fluorinated alkyl group, or a partially or completely fluorinated phenyl group;
each of the $R'^2$ and $R'^3$ groups represents R or F;
wherein:
several R or $R_F$ groups can be linked together so as to form a segment of an oligomer or of a polymer;
in a ID and IID complex, if two groups among —$X^1$—, —$X^2$— and —$X^3$— each represent >C=O, then the third group represents a >$CR^2R^3$ group;
in a ID complex, if each of the $X^1$, $X^2$ and $X^3$ groups is a $CH_2$ group and each of the Y groups is O, then $R^1$ is other than $CH_3$.

2. The complex as claimed in claim 1, wherein each of the $Y^1$, $Y^2$ and $Y^3$ groups represents O.

3. The complex as claimed in claim 1, wherein at least one of the $Y^1$, and $Y^2$ $Y^3$ groups represents NR$^4$.

4. The complex as claimed in claim 2, wherein $R^1$ is selected from the group consisting of R$_F$SO$_2$—, NO$_2$, RSO$_2$—, —CN and —C(=O)OR, and/or at least one of the —$X^1$—, —$X^2$— and —$X^3$—, and where appropriate $X^4$, groups represents a group chosen from >C=O, >C=NC=N, >C=C(C=N)$_2$ and SO$_2$, just one among the —$X^1$—, —$X^2$— and —$X^3$— groups being SO$_2$.

5. The complex as claimed in claim 3, wherein at least one of the —$X^1$—, —$X^2$— and —$X^3$—, and where appropriate $X^4$— groups represents a group selected from the group consisting of >C=O, >C=NC=N and >C=C(C=N)$_2$.

6. The complex as claimed in claim 1, wherein each of the —$X^1$—, —$X^2$— and —$X^3$—, and where appropriate $X^4$, groups represents a $CR^2R^3$ group.

7. The complex as claimed in claim 1, wherein at least one of the $Y^1$, $Y^2$ and $Y^3$ groups is selected from the group consisting of N(C=N), >N(COR$_F$), >N(SO$_2$R$^4$), >N(COR$^4$), >N(SO$_2$R$_F$) or an >NR$^4$ group in which R$^4$ is an aryl or heteroaryl bearing at least one withdrawing group and/or the $R^1$ group is selected from the group consisting of R$_F$SO$_2$—, NO$_2$, RSO$_2$—, —CN and —C(=O)OR.

8. An adduct formed by a salt $M_zZ'_m$ complexed with a complex as claimed in claim 1, in which M is a cation of which the valence n is from 1 to 3, and Z' is an anion of which the valence z' is 1 or 2.

9. The adduct as claimed in claim 8, wherein Z' is a monovalent anion chosen from the anions F$^-$, Cl$^-$, Br$^-$, OCN$^-$, O$_2^{2-}$, O$_2^{\cdot-}$, OH$^-$, RO$^-$, N$_3^-$, CN$^-$, [O$^{2-}$M'$^+$]$^-$, [O$_2^{2-}$M'$^+$]$^-$ and [NCN$^{2-}$M'$^+$], M' being H or a monovalent cation.

10. The adduct as claimed in claim 8, wherein Z' is a divalent anion chosen from the anions O$^{2-}$, O$_2^{2-}$, S$^{2-}$, S$_2^{2-}$ and NCN$^{2-}$.

11. The adduct as claimed in claim 8, wherein M represents an alkaline metal cation, an alkaline-earth metal cation, Ag$^+$, Pb$^{2+}$, an yttrium cation, a lanthanum cation or an organic cation.

12. The adduct as claimed in claim 11, wherein M is an organic cation selected from the group consisting of ammonium, phosphonium, tetrakis(dialkylamino)phosphonium, bis[tris(dialkylamino)]diphosphonioazenium, sulfonium, pyridinium, amidinium, guanidinium, imidazolium, pyrazolium and triazolium cations, said organic cations optionally bearing a substituent chosen from alkyl, oxaalkyl, aryl, alkylaryl and arylalkyl groups, it being possible for said cations to be linked to one another via an organic linker so as to form oligomers or polymers.

13. A method for the production of a lithium battery, said method comprising the step of:
applying said polycyclic complex as claimed in claim 1, as an additive of an electrolyte.

14. The method as claimed in claim 13, wherein at least one of the $Y^1$, $Y^2$ and $Y^3$ groups is a nitrogenous group other than NR$^4$, or else at least one of the $X^1$, $X^2$ and $X^3$ groups is a C=NCN or C=C(CN)$_2$ group.

15. A process for modifying a compound having a Cl or Br atom, by means of a nucleophilic substitution reaction, wherein said process uses, as reactant, an adduct as claimed in claim 8.

16. The process as claimed in claim 15, wherein the compound is a solid compound selected from the group consisting of the inorganic compounds with a lamellar structure FeOCl, VOCl, BiOCl, BiONO$_3$, TiNCl, TiNBr, ZrNCl or ZrNBr, or a liquid compound selected from the group consisting of $\{[CF_3SO_2NSO_2Cl]^-\}_nM^{n+}$, $\{[(ClSO_2)_2N]^-\}_nM^{n+}$ and $\{[(Cl_2PO)_2N]^-\}_nM^{n+}$.

17. A process for modifying an aliphatic or aromatic organic compound which has a C-L bond in which C is carbon and L is a halogen selected from the group consisting of Cl, Br and I, a pseudohalogen, an ester group —OSO$_2$R' or an —N(SO$_2$R')$_2$ group, in which R' is an alkyl group, an alkylaryl group or a perfluoroalkyl group, wherein said organic compound is reacted with an adduct as claimed in claim 8.

18. A process for deprotecting a trialkylsilane group in an organic compound, wherein said process includes bringing said organic compound into contact with an adduct as claimed in claim 8, in which Z is F.

19. A process for modifying a compound having a Cl or Br atom, by means of a nucleophilic substitution reaction, wherein said process uses, as reactant, an adduct as claimed in claim 8, prepared in situ.

* * * * *

UNITED STATES PATENT AND TRADEMARK OFFICE
CERTIFICATE OF CORRECTION

PATENT NO.        : 8,563,761 B2                                Page 1 of 1
APPLICATION NO.   : 12/736195
DATED             : October 22, 2013
INVENTOR(S)       : Armand et al.

It is certified that error appears in the above-identified patent and that said Letters Patent is hereby corrected as shown below:

In the Claims

Column 57, Claim 3, Line 49: "Y2 Y3" between the words "and" and "groups" should read: "$Y^2$ and $Y^3$"

Signed and Sealed this
Seventh Day of January, 2014

Margaret A. Focarino
*Commissioner for Patents of the United States Patent and Trademark Office*